(12) United States Patent
Dwivedi et al.

(10) Patent No.: US 9,409,899 B2
(45) Date of Patent: Aug. 9, 2016

(54) PROCESS FOR PREPARING BENZISOTHIAZOL-3-YL-PIPERAZIN-1-YL-METHYL-CYCLO HEXYLMETHANISOINDOL-1,3-DIONE AND ITS INTERMEDIATES

(71) Applicant: Cadila Healthcare Limited, Ahmedabad (IN)

(72) Inventors: Shri Prakash Dhar Dwivedi, Ahmedabad (IN); Ramesh Chandra Singh, Ahmedabad (IN); Rajendra Gokalbhai Chavda, Ahmedabad (IN)

(73) Assignee: Cadila Healthcare Limited (IN)

( * ) Notice: Subject to any disclaimer, the term of this patent is extended or adjusted under 35 U.S.C. 154(b) by 0 days.

(21) Appl. No.: 14/378,303

(22) PCT Filed: Feb. 12, 2013

(86) PCT No.: PCT/IN2013/000091
§ 371 (c)(1),
(2) Date: Aug. 12, 2014

(87) PCT Pub. No.: WO2013/121440
PCT Pub. Date: Aug. 22, 2013

(65) Prior Publication Data
US 2015/0018368 A1  Jan. 15, 2015

(30) Foreign Application Priority Data

Feb. 13, 2012  (IN) .............................. 392MUM2012
Sep. 6, 2012   (IN) .......................... 2589/MUM/2012

(51) Int. Cl.
*C07D 417/12* (2006.01)
*C07D 487/10* (2006.01)
*C07C 51/347* (2006.01)
*C07C 51/36* (2006.01)
*C07C 51/43* (2006.01)
*C07C 51/02* (2006.01)
*C07C 51/353* (2006.01)
*C07C 51/41* (2006.01)

(52) U.S. Cl.
CPC .............. *C07D 417/12* (2013.01); *C07C 51/02* (2013.01); *C07C 51/347* (2013.01); *C07C 51/353* (2013.01); *C07C 51/36* (2013.01); *C07C 51/412* (2013.01); *C07C 51/43* (2013.01); *C07D 487/10* (2013.01); *Y10T 428/2982* (2015.01)

(58) Field of Classification Search
CPC ........................... C07D 417/12; C07D 487/10
USPC .............................. 544/231, 368; 514/254.04
See application file for complete search history.

(56) References Cited

U.S. PATENT DOCUMENTS

| | | |
|---|---|---|
| 5,532,372 A | 7/1996 | Saji et al. |
| 7,605,260 B2 | 10/2009 | Kakiya et al. |
| 2009/0285805 A1 | 11/2009 | Grosveld et al. |
| 2011/0021103 A1 | 1/2011 | Alper et al. |
| 2011/0263847 A1 | 10/2011 | Ae et al. |

FOREIGN PATENT DOCUMENTS

| | | |
|---|---|---|
| EP | 0464846 A1 | 1/1992 |
| FR | 2262652 A1 | 9/1975 |
| WO | WO 0176557 A1 * | 10/2001 |
| WO | WO-2011093522 A1 | 8/2011 |
| WO | WO-2011136383 A1 | 11/2011 |
| WO | WO-2011136384 A1 | 11/2011 |
| WO | WO-2012016569 A1 | 2/2012 |
| WO | WO-2012063246 A1 | 5/2012 |
| WO | WO-2012107890 A2 | 8/2012 |
| WO | WO-2012123858 A1 | 9/2012 |
| WO | WO-2012131606 A1 | 10/2012 |
| WO | WO-2013121440 A1 | 8/2013 |

OTHER PUBLICATIONS

"International Application Serial No. PCT/IN2013/000091, International Preliminary Report on Patentability mailed Aug. 28, 2014", 13 pgs.
"International Application Serial No. PCT/IN2013/000091, Written Opinion mailed Jul. 25, 2013", 11 pgs.
"International Application Serial No. PCT/IN2013/000091, International Search Report mailed Jul. 25, 2013", 6 pgs.
Berkessel, Albrecht, et al., "Enantiomerically Pure [beta]-Amino Acids: A Convenient Access to Both Enantiomers of trans-2-Aminocyclohexanecarboxylic Acid", Eur. J. Org. Chem., (Jan. 1, 2002), 2948-2952.
Cole, P., et al., "Lurasidone hydrochloride: dopamine D2/5-HT2A antagonist treatment of schizophrenia", Drugs of the Future 33(4), (2008), 316-322.
Goodridge, Richard J, et al., "Preparations and crystal structures of the 2-oxides of some octahydro-3,2,1-benzoxathiazines and octahydro-2H-3,1,2-benzoxazaphosphorines", Australian Journal of Chemistry, 39(4), (1986), 591-604.
Hufford, Duane L, et al., "Maleic and Fumaric Dialdehydes, ?4-Tetrahydrophthalaldehyde and Related Compounds", Journal of the American Chemical Society, 74(12), (Jun. 20, 1952), 3014-3018.

* cited by examiner

*Primary Examiner* — Kahsay Habte
(74) *Attorney, Agent, or Firm* — Schwegman, Lundberg & Woessner, P.A.

(57) ABSTRACT

The present invention discloses process for preparing benzisothiazol-3-yl-piperazin-1-yl-methyl-cyclohexyl-methanisoindol-1,3-dione and intermediates thereof.

27 Claims, 6 Drawing Sheets

Figure 1:
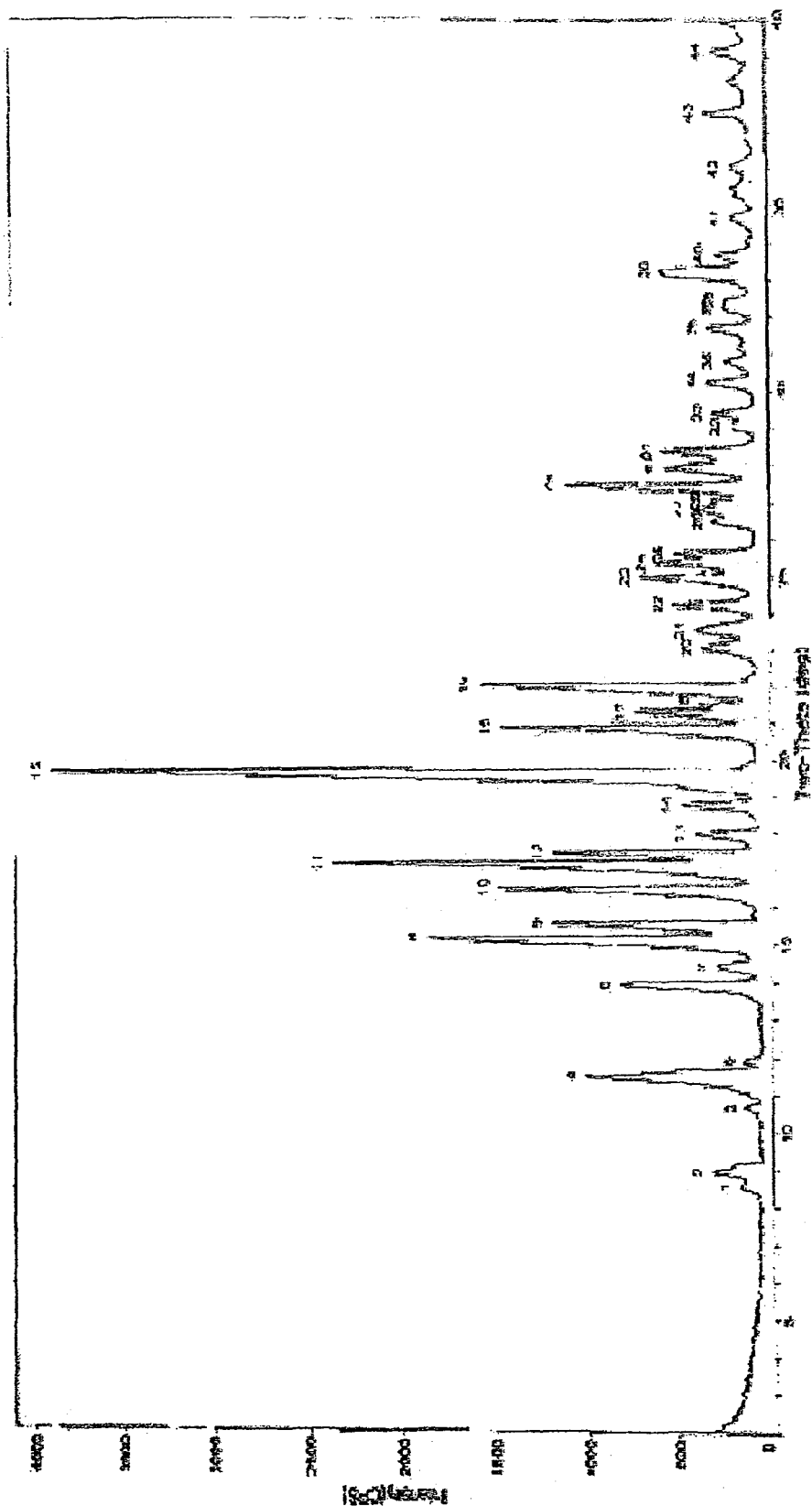

PROCESS FOR PREPARING BENZISOTHIAZOL-3-YL-PIPERAZIN-1-YL-METHYL-CYCLO HEXYLMETHANISOINDOL-1,3-DIONE AND ITS INTERMEDIATES

PRIORITY APPLICATIONS

This application is a U.S. National Stage Filing under 35 U.S.C. 371 from International Application No. PCT/IN2013/000091, filed on 12 Feb. 2013, and published as WO 2013/121440 A1 on 22 Aug. 2013, which claims the benefit of priority to Indian Application No. 392/MUM/2012, filed on 13 Feb. 2012, and also claims the benefit of priority to Indian Application No. 2589/MUM/2012, filed on 6 Sep. 2012; which applications and publication are incorporated herein by reference in their entirety.

FIELD OF THE INVENTION

The present invention relates to process for preparing benzisothiazol-3-yl-piperazin-1-yl-methyl-cyclo hexyl-methanisoindol-1,3-dione and intermediates thereof. In particular, the present invention relates to crystalline form lurasidone free base of Formula (H) and intermediate of Formula (G). More particularly, the present invention relates to process for the preparation of intermediates of Formula (B), Formula (C), Formula (E) and Formula (I). The invention also relates to the use of intermediates prepared by the process of the present invention to prepare lurasidone hydrochloride of Formula (1).

BACKGROUND OF THE INVENTION

Lurasidone is a well-known dopaminergic (D2) and serotonin. (5-HT2A) receptor antagonist and is disclosed in U.S. Pat. Nos. 5,780,632 and 5,532,372. Lurasidone is the INN of a psychotropic compound (3aR,4S,7R,7aS)-2-[((1R,2R)-2-{[4-(1,2-benzisothiazol-3-yl)-piperazin-1-yl]methyl}cyclohexyl)methyl]hexahydro-1H-4,7-methanisoindol-1,3-dione hydrochloride represented by Formula (1).

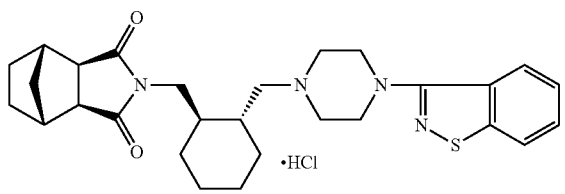

(1)

A free form of lurasidone and an acid addition salt thereof are known to have psychotropic activities and are effective as therapeutic agents, particularly for schizophrenia or senile dementia, etc. Senile dementia is broadly classified into Alzheimer's dementia and cerebrovascular dementia, and it can be said that the two make up about 80% of senile dementia.

U.S. Pat. No. 5,532,372 discloses (3aR,4S,7R,7aS)-2-[((1R,2R)-2-{[4-(1,2-benzisothiazol-3-yl)-piperazin-1-yl]methyl}cyclohexyl)methyl]hexahydro-1H-4,7-methanisoindol-1,3-dione or its pharmaceutically acceptable salts and process for preparing thereof.

U.S. Pat. No. 7,605,260 B2 discloses process for preparing (3aR,4S,7R,7aS)-2-[((1R,2R)-2-{[4-(1,2-benzisothiazol-3-yl)-piperazin-1-yl]methyl}cyclohexyl)methyl]hexahydro-1H-4,7-methanisoindol-1,3-dione hydrochloride of Formula (1) from free base of 3aR,4S,7R,7aS)-2-[((1R,2R)-2-{[4-(1,2-benz isothiazol-3-yl)-piperazin-1-yl]methyl}cyclohexyl)methyl]hexahydro-1H-4,7-methanisoindol-1,3-dione using 1.8 to 5% aqueous hydrochloric acid solution in acetone.

U.S. Patent Publication No. US 2009/0285805 discloses a solution-type preparation of lurasidone or acid addition salt thereof prepared by incorporating one or more substances selected from benzyl alcohol, N,N-dimethylacetamide, lactic acid, anhydrous ethanol and propylene glycol.

International (PCT) Publication WO 2011/093522 A1 discloses cycloalkane derivative having a steric configuration of (3aR,4S,7R,7aS)-2-[((1R,2R)-2-{[4-(1,2-benzisothiazol-3-yl)-piperazin-1-yl]methyl}cyclohexyl)methyl]hexahydro-1H-4,7-methanisoindol-1,3-dione or its pharmaceutically acceptable salts, which was not disclosed in U.S. Pat. No. 5,532,372.

International (PCT) Publications WO 2011/136383 A1 and WO 2011/136384 A1 discloses process for preparing Lurasidone and intermediates thereof.

International (PCT) Publications WO 2012/123858 A1 and WO 2012/063246 A1 discloses amorphous form of lurasidone hydrochloride and process for its preparation.

International (PCT) Publication WO 2012/107890 A2 discloses crystalline forms of lurasidone hydrochloride and processes for its preparation.

International (PCT) Publication WO 2012/131606 A1 (the WO '606 A1) and *J. Mol. Catalysis. A: Chemical*, Vol. 206 (1-2) Pg. 95-103 (2003) discloses the process for the preparation of (1R,2R)-cyclohexane-1,2-diylbis(methylene) dimethanesulfonate of Formula (B).

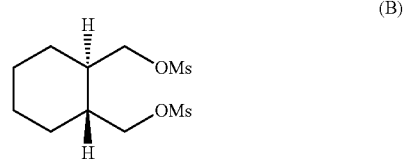 [SMILES: CS(=O)(=O)OC[C@@H]1CCCC[C@H]1COS(C)(=O)=O]

(B)

The WO '606 A1 also discloses the process for the preparation of (3aR,7aR)-4'-(benzo[d]isothiazole-3-yl)octahydrospiro]isoindole-2,1'-piperazin]-1'-ium mesylate of Formula (G) by reacting (1R,2R)-cyclohexane-1,2-diylbis (methylene)dimethanesulfonate of Formula (B) and 3-(piperazin-1-yl)benzo[d]isothiazole of Formula (F) in presence of base and a solvent.

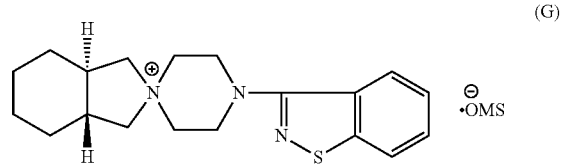 [SMILES: c1ccc2c(N3CC[N+]4(CC3)C[C@@H]3CCCC[C@H]3C4)nsc2c1]

(G)

International (PCT) publication WO 2011/002103 A1, IP.com Journal, 11(4A), 5; 2011, U.S. Patent Appl. Pub. No. 2011/0263847 A1 and European Patent EP 464846 B1 discloses various processes for the preparation of (3aR,7aR)-4'-(benzo[d]isothiazole-3-yl)octahydrospiro]isoindole-2,1'-piperazin]-1'-ium mesylate of Formula (G), which are herein cited as the reference in their entirety.

*IP.com Journal* Vol. 11(4A) Pg 5 (2011) discloses crystalline form of (3aR,7aR)-4'-(benzo[d]isothiazole-3-yl)octahydrospiro]isoindole-2,1'-piperazin]-1'-ium mesylate of Formula (G) characterized by x-ray powder diffraction pattern having peaks at 7.6°, 9.1°, 16.2°, 16.9°, 18.9°, 19.2°, 20.2° and 25.0°±0.2 2θ.

*IP.com Journal* Vol. 11(4A) Pg 26 (2011) discloses crystalline form of lurasidone free base of Formula (H) characterized by x-ray powder diffraction pattern having peaks at 11.3°, 14.1°, 15.2°, 15.7°, 16.4°, 16.7°, 18.1°, 19.2°, 20.1° and 22.4°±0.2 2θ.

International (PCT) Publication WO 2012/016569 A1 discloses the process for the preparation of (3aS,4R,7S,7aR)-hexahydro-4,7-methano-1H-isoindole-1,3-(2H)-dione of Formula (E) by reducing bicyclo[2.2.1]hept-5-ene-2-oxo-3-exo-dicarboxlyic acid anhydride of Formula (C) followed by reaction with aqueous ammonia.

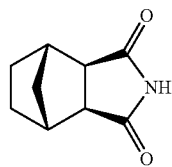

(E)

The prior art discloses the process for the preparation of lurasidone hydrochloride and its intermediates. However, there still remains a need for alternative process for the preparation of intermediates of lurasidone and their crystalline forms, thereby providing an improved process for the preparation of lurasidone hydrochloride of Formula (1).

SUMMARY OF THE INVENTION

In one general aspect, there is provided a process for preparing (1R,2R)-(−)-trans-cyclohexane-1,2-dicarboxylic acid of Formula (I), intermediate for lurasidone hydrochloride of Formula (1),

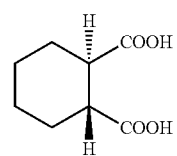

(I)

the process comprising:
(a) reacting butadienesulfolane of Formula (J) with fumaric acid in presence of an acid to obtain trans-cyclohexene-1,2-dicarboxylic acid (L);

(J)

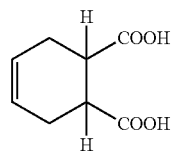

(L)

(b) reducing trans-cyclohexene-1,2-dicarboxylic acid of Formula (L) to obtain racemic (1R,2R)-transcyclohexane-1,2-dicarboxylic acid of Formula (M);

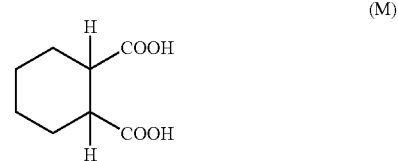 [SMILES: O=C(O)C1CCCCC1C(=O)O]

(M)

(c) resolving (1R,2R)-trans-cyclohexane-1,2-dicarboxylic acid of Formula (M) with (R)-α-methyl benzylamine to obtain (R)-α-methyl benzylamine salt of (1R,2R)-trans-cyclohexane-1,2-dicarboxylic acid of Formula (N); and

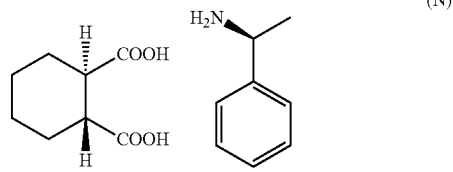

(N)

(d) treating (R)-α-methyl benzylamine salt of (1R,2R)-(−)-trans-cyclohexane-1,2-dicarboxylic acid (N) with an acid to obtain (1R,2R)-(−)-trans-cyclohexane-1,2-dicarboxylic acid of Formula (I).

In another general aspect, there is provided crystalline form of (3aR,7aR)-4'-(benzo[d]isothiazol-3-yl)octahydrospiro[isoindole-2,1'-piperazin]-1'-ium mesylate of Formula (G).

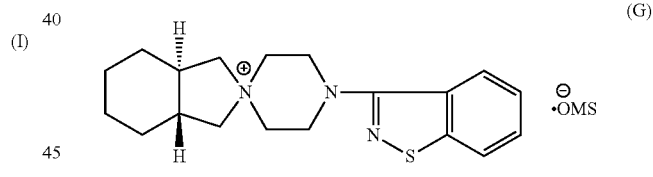

(G)

In another general aspect, there is provided a crystalline form of (3aR,7aR)-4'-(benzo[d]isothiazol-3-yl)octahydrospiro[isoindole-2,1'-piperazin]-1'-ium mesylate of Formula (G) characterized by X-ray powder diffraction (XRD) and DSC.

In another general aspect, there is provided a process for preparing crystalline form of (3aR,7aR)-4'-(benzo[d]isothiazol-3-yl)octahydrospiro[isoindole-2,1'-piperazin]-1'-ium mesylate of Formula (G),

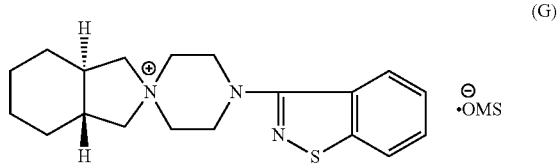 [SMILES: c1ccc2c(N3CC[N+]4(CC3)C[C@@H]3CCCC[C@H]3C4)nsc2c1]

(G)

the process comprising reacting (1R,2R)-cyclohexane-1,2-diylbis(methylene)dimethanesulfonate of Formula (B)

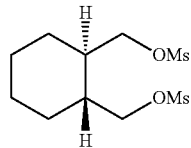
(B)

with 3-(piperazin-1-yl)benzo[d]isothiazole of Formula (F)

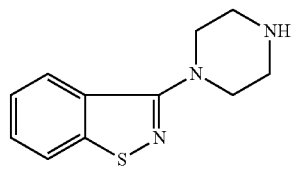
(F)

in presence of base and a phase transfer catalyst in one or more of suitable solvent to obtain (3aR,7aR)-4'-(benzo[d]isothiazol-3-yl)octahydrospiro[isoindole-2,1'-piperazin]-1'-ium mesylate of Formula (G) and obtaining crystalline (3aR,7aR)-4'-(benzo[d]isothiazol-3-yl)octahydrospiro-[isoindole-2,1'-piperazin]-1'-ium mesylate by removal of solvent.

In another general aspect, there is provided crystalline form of lurasidone free base of Formula (H)

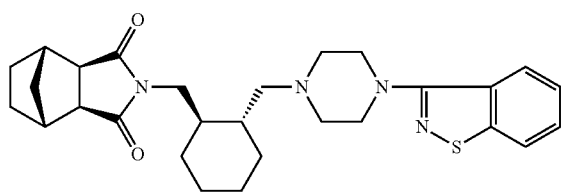
(H)

In another general aspect, there is provided a crystalline form of lurasidone free base of Formula (H) characterized by X-ray powder diffraction (XRD) and DSC.

In another general aspect, there is provided a process for preparing crystalline form of lurasidone free base of Formula (H),

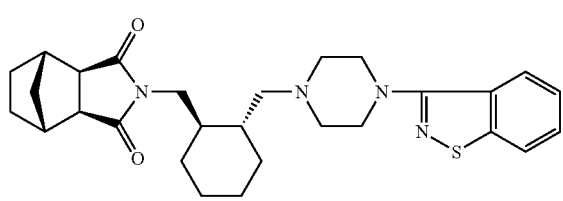
(H)

the process comprising reacting (3aR,7aR)-4'-(benzo[d]isothiazol-3-yl)octahydrospiro[isoindole-2,1'-piperazin]-1'-ium mesylate of Formula (G)

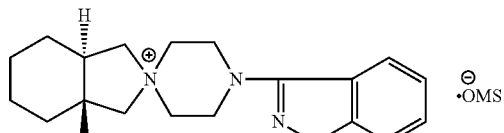
(G)

with bicyclo[2.2.1]heptane-2-exo-3exo-dicarboximide of Formula (E)

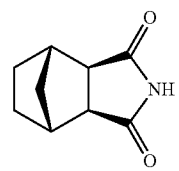
(E)

in presence of base and phase transfer catalyst in one or more of suitable organic solvent to obtain lurasidone free base and obtaining crystalline form of lurasidone free base of Formula (H) by removal of solvent.

In another general aspect, there is provided use of crystalline form of (3aR,7aR)-4'-(benzo[d]isothiazol-3-yl)octahydrospiro[isoindole-2,1'-piperazin]-1'-ium mesylate of Formula (G) in the preparation of lurasidone hydrochloride of Formula (1). In another general aspect, there is provided use of crystalline form of lurasidone free base of Formula (H) in the preparation of lurasidone hydrochloride of Formula (1).

In another general aspect, there is provided crystalline form of lurasidone hydrochloride represented by Formula (1).

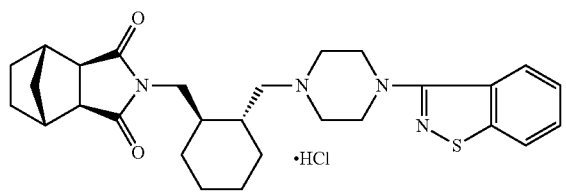
(1)

In another general aspect, there is provided a crystalline form of lurasidone hydrochloride of Formula (1) characterized by X-ray powder diffraction (XRD) and DSC.

In another general aspect, there is provided a process for preparation of crystalline form of lurasidone hydrochloride of Formula (1),

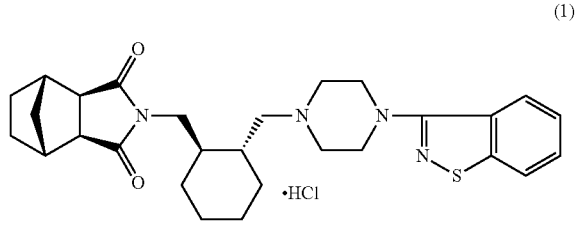
(1)

the process comprising:
(a) reacting (3 aR,7aR)-4'-(benzo[d]isothiazol-3-yl)octahydrospiro[isoindole-2,1'-piperazin]-1'-ium mesylate of Formula (G) and bicyclo[2.2.1]heptane-2-exo-3-exo-dicarboximide of Formula (E) in presence of base and a phase transfer catalyst in one or more of suitable organic solvent to obtain lurasidone free base of Formula (H);
(b) reacting lurasidone free base of Formula (H) with hydrochloric acid source in one or more of suitable solvent to obtain lurasidone hydrochloride; and
(c) obtaining crystalline form of lurasidone hydrochloride of Formula (1).

In another general aspect, there is provided a process for preparation of lurasidone hydrochloride of Formula (1),

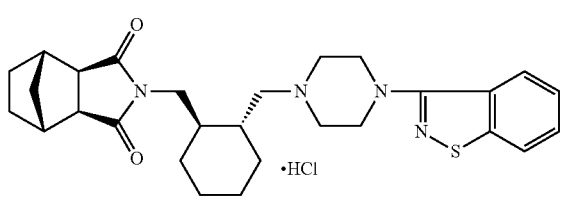
(1)

the process comprising:
(a) reducing (1R,2R)-(−)-trans-cyclohexane-1,2-dicarboxylic acid with a suitable reducing agent in one or more of suitable organic solvent to obtain (1R,2R)-(−)-trans-cyclohexane-1,2-diyldimethanol of Formula (A);
(b) reacting (1R,2R)-(−)-trans-cyclohexane-1,2-diyldimethanol of Formula (A) with methanesulfonyl chloride in presence of base in one or more of suitable organic solvent to obtain (1R,2R)-(−)-trans-cyclohexane-1,2-diylbis(methylene)dimethanesulfonate of Formula (B);
(c) reacting (1R,2R)-(−)-trans-cyclohexane-1,2-diylbis(methylene)dimethanesulfonate of Formula (B) and 3-(piperazin-1-yl)benzo[d]isothiazole of Formula (F) in presence of base and a phase transfer catalyst in one or more of suitable organic solvent to obtain crystalline form of (3aR,7aR)-4'-(benzo[d]isothiazol-3-yl)octahydrospiro[isoindole-2,1'-piperazin]-1'-ium mesylate of Formula (G);
(d) reacting crystalline form of (3aR,7aR)-4'-(benzo[d]isothiazol-3-yl)octahydrospiro[isoindole-2,1'-piperazin]-1'-ium mesylate of Formula (G) with (3aS,4R,7S,7aR)-hexahydro-4,7-methano-1H-isoindole-1,3-(2H)-dione of Formula (E) in presence of base and a phase transfer catalyst in one or more of suitable organic solvent to obtain crystalline form of lurasidone free base of Formula (H);
(e) reacting crystalline form of lurasidone free base of Formula (H) with hydrochloric acid source in one or more of suitable organic solvent to obtain lurasidone hydrochloride of Formula (1); and
(f) obtaining crystalline form of lurasidone hydrochloride of Formula (1) by removal of solvent.

In another general aspect, there is provided lurasidone hydrochloride of Formula (1) having a total purity of greater than about 99%, particularly greater than about 99.5%, more particularly greater than about 99.9%, and most particularly greater than about 99.98% as measured by HPLC.

In another general aspect, there is provided lurasidone hydrochloride having particle size of d(90) less than about 100 microns.

In another general aspect, there is provided microcrystalline lurasidone hydrochloride having particle size of d(90) less than about 10 microns.

BRIEF DESCRIPTION OF THE ACCOMPANYING DRAWINGS

FIG. 1. Shows X-ray diffractogram (XRD) of crystalline form of lurasidone hydrochloride of Formula (1).

Figure 2:

FIG. 2. Shows Differential Scanning calorimetry (DSC) of crystalline form of lurasidone hydrochloride of Formula (1).

Figure 3:
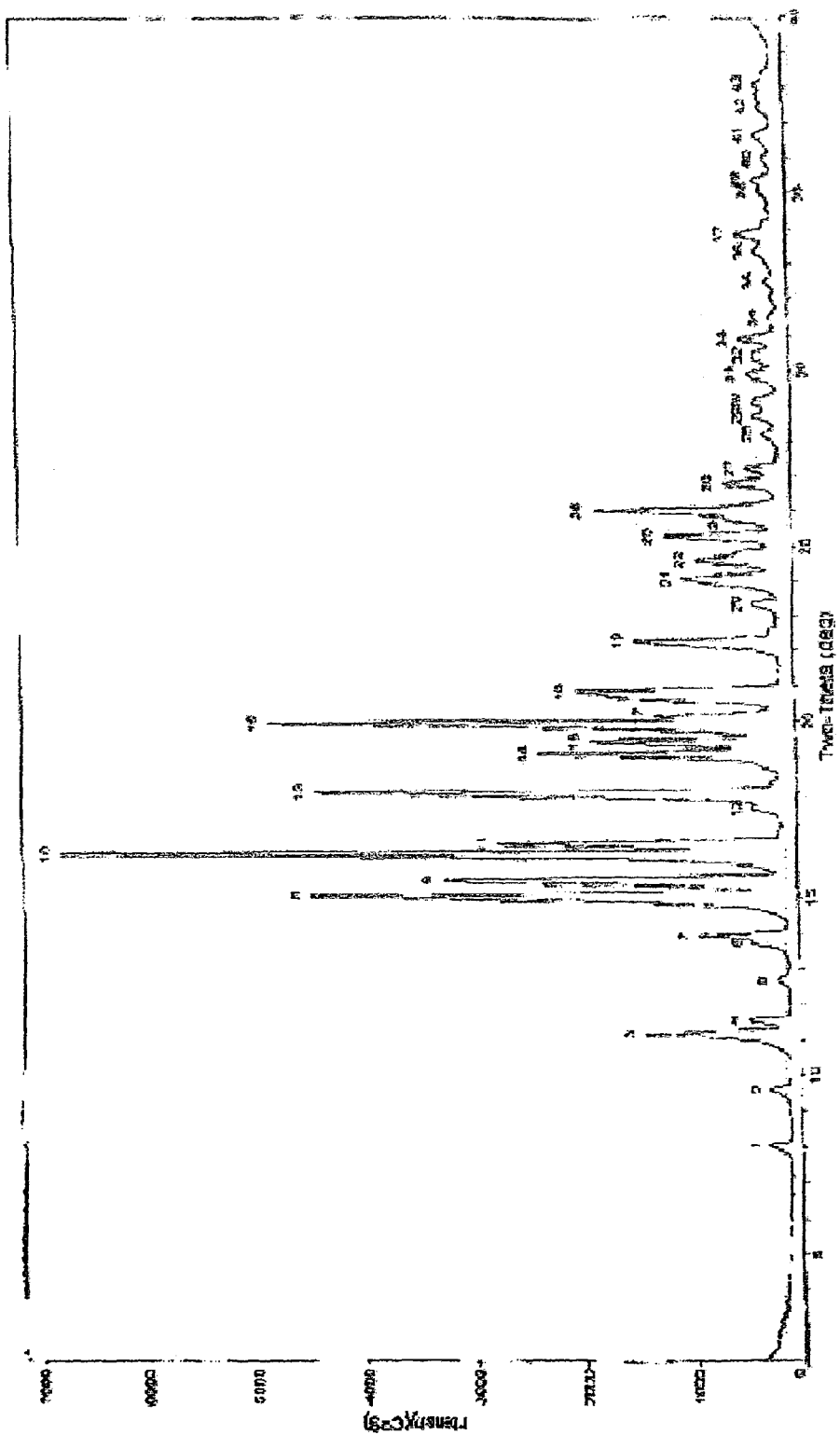

FIG. 3. Shows X-ray diffractogram (XRD) of crystalline form of lurasidone free base of Formula (H).

Figure 4:
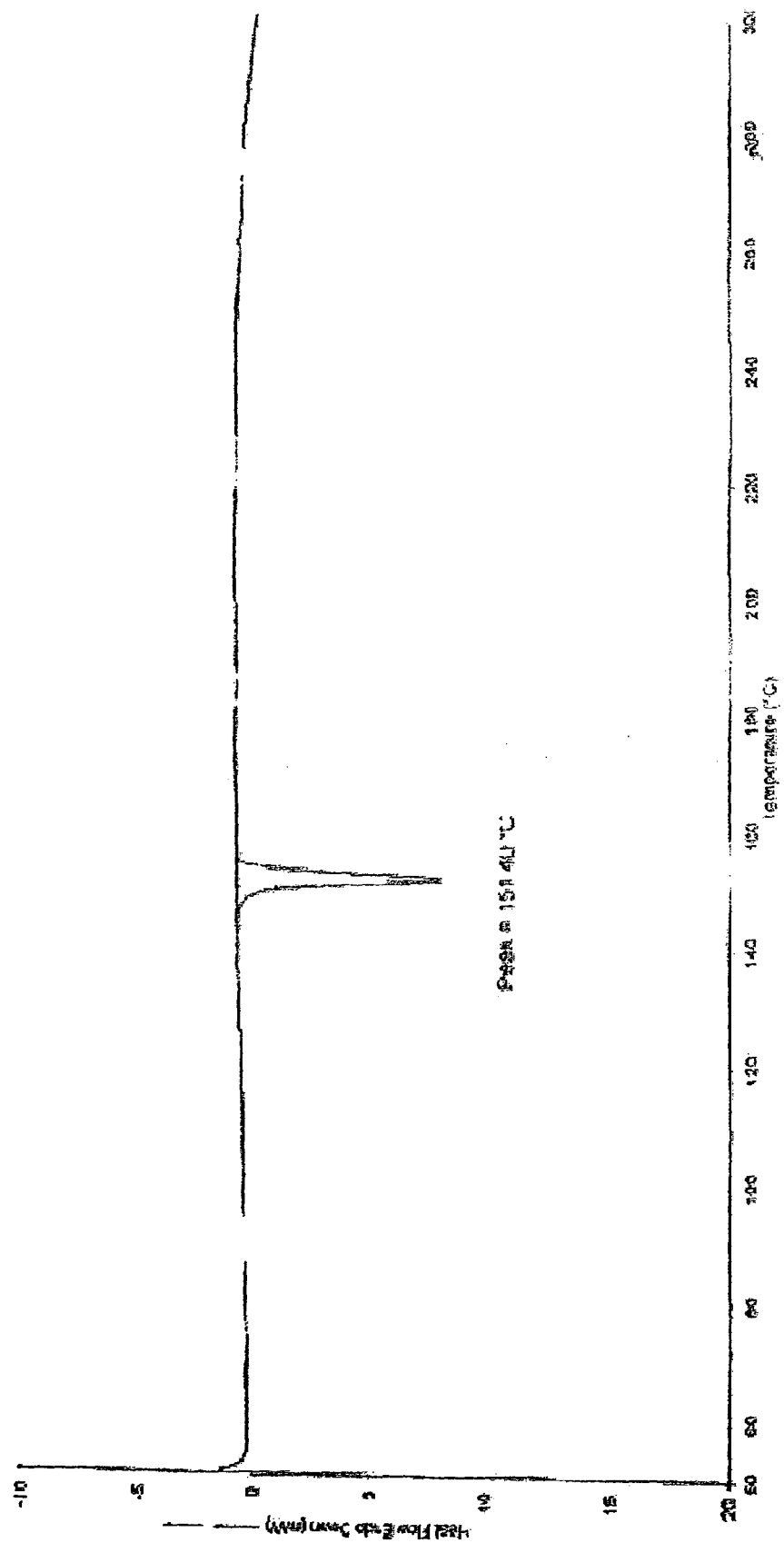

FIG. 4. Shows Differential Scanning calorimetry (DSC) of crystalline form of lurasidone free base of Formula (H).

Figure 5:
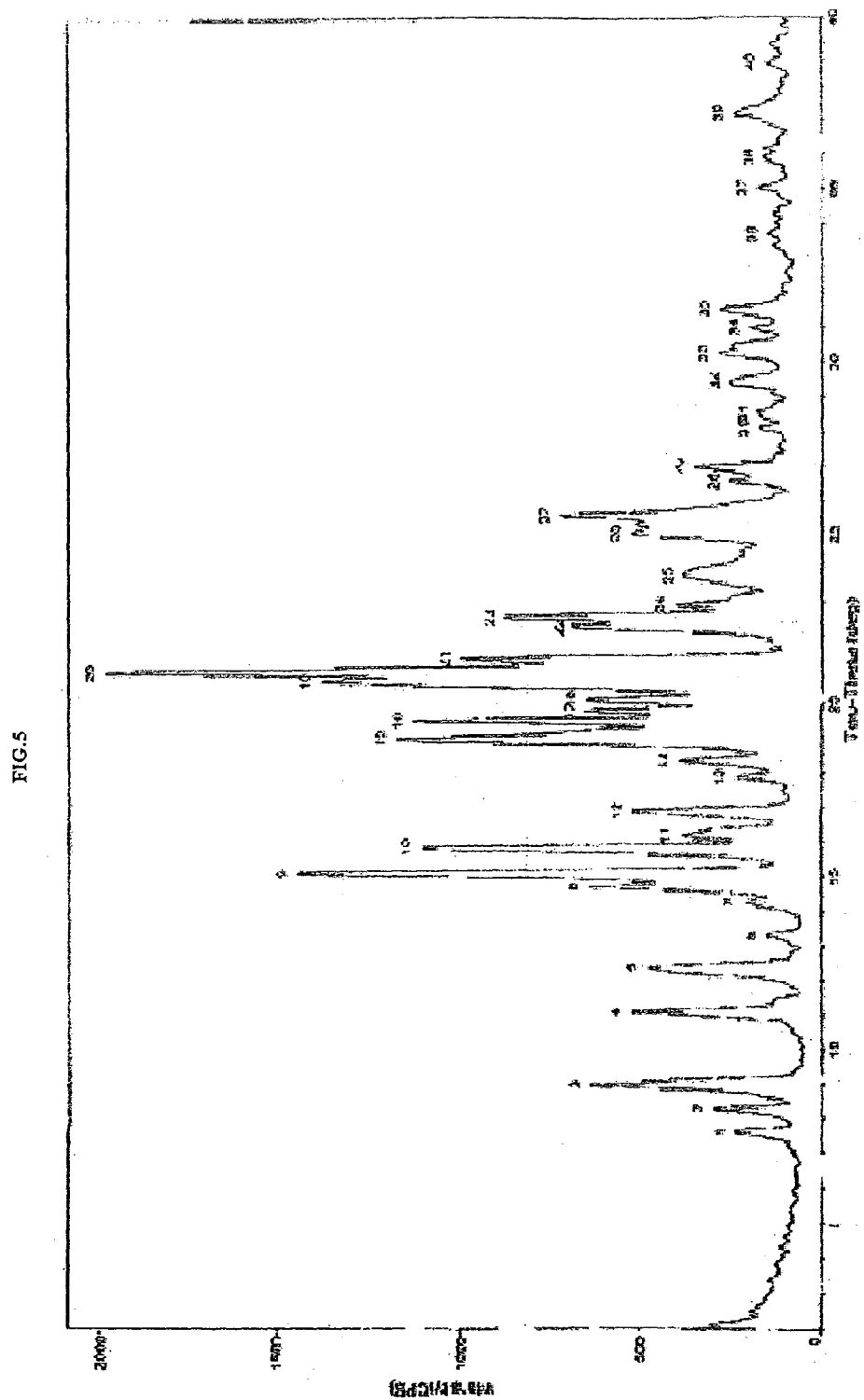

FIG. 5. Shows. X-ray diffractogram (XRD) of crystalline form of (3aR,7aR)-4'-(benzo[d]isothiazol-3-yl)octahydrospiro[isoindole-2,1'-piperazin]-1'-ium mesylate of Formula (G).

Figure 6:
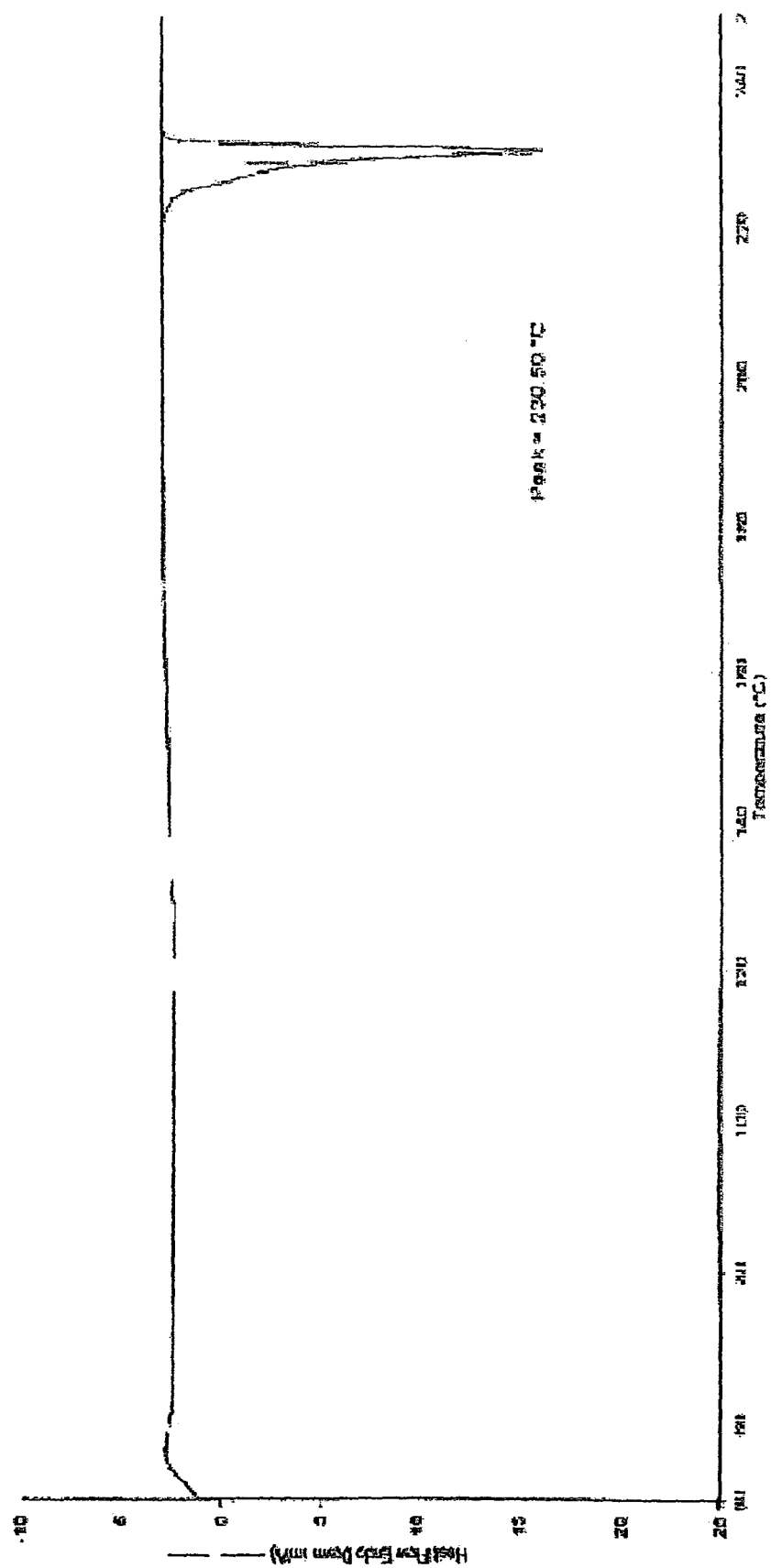

FIG. 6. Shows Differential Scanning calorimetry (DSC) of crystalline form of (3aR, 7aR)-4'-(benzo[d]isothiazol-3-yl)octahydrospiro[isoindole-2,1'-piperazin]-1'-ium mesylate of Formula (G).

DETAILED DESCRIPTION OF INVENTION

The terms such as "about", "generally", "substantially," and the like are to be construed as modifying a term or value such that it is not an absolute. Such terms will be defined by the circumstances and the terms that they modify as those terms are understood by those skill in the art. This includes, at very least, the degree of expected experimental error, technique error and instrument error for a given technique used to measure a value.

As used herein, the terms "obtaining" means isolating by way of removal of solvent. The known techniques like filtration, filtration under vacuum, centrifugation, decantation and the like may be used. The product obtained may be further or additionally dried to achieve the desired moisture values. For example, the product may be dried in a tray drier, dried under vacuum and/or in a Fluid Bed Drier.

In one general aspect, there is provided a process for preparing (1R,2R)-(−)-trans-cyclohexane-1,2-dicarboxylic acid of Formula (I), intermediate for lurasidone hydrochloride of Formula (1),

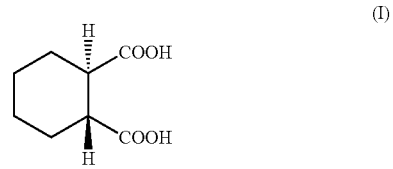 [SMILES: O=C(O)[C@@H]1CCCC[C@H]1C(=O)O]
(I)

the process comprising:
(a) reacting butadienesulfolane of Formula (J) with fumaric acid in presence of an acid to obtain trans-cyclohexene-1,2-dicarboxylic acid (L);

(J)

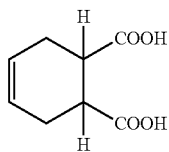

(L)

(b) reducing trans-cyclohexene-1,2-dicarboxylic acid of Formula (L) to obtain racemic (1R,2R)-transcyclohexane-1,2-dicarboxylic acid of Formula (M);

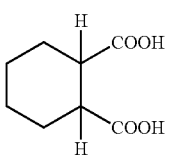

(M)

(c) resolving (1R,2R)-trans-cyclohexane-1,2-dicarboxylic acid of Formula (M) with (R)-α-methyl benzylamine, to obtain (R)-α-methyl benzylamine salt of (1R,2R)-trans-cyclohexane-1,2-dicarboxylic acid of Formula (N); and

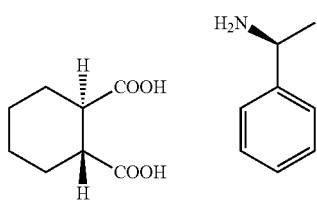

(N)

(d) treating (R)-α-methyl benzylamine salt of (1R,2R)-(−)-trans-cyclohexane-1,2-dicarboxylic acid (N) with an acid to obtain (1R,2R)-(−)-trans-cyclohexane-1,2-dicarboxylic acid of Formula (I).

In general, the reaction step (a) may be performed in one or more of suitable solvent comprises of $C_1$-$C_5$ alcohols, esters, ethers, ketones, water or a mixture thereof. In particular, methanol, ethanol, isopropanol, butanol, t-butanol, ethyl acetate, isopropyl acetate, butylacetate, tetrahydrofuran, 1,4-dioxaone, 2-methyl tetrahydrofuran, acetone, methyl ethyl ketone, methyl isobutyl ketone, water may be used. More particularly, acetone is the preferred solvent. The suitable acid used in step (a) may be selected from hydrochloric acid, acetic acid, sulfuric acid, trifluoroacetic acid and the like. In particular, acetic acid may be used.

The embodiment of the process further includes reduction of compound of Formula (L). The reduction may be performed in suitable solvent. The suitable solvent in step (b) comprises one or more of water, hydrocarbons, nitriles, amides, alcohols, halogenated solvents, ketones, esters, ethers and the like. In particular, the suitable solvent comprises toluene, xylene, ethylbenzene, dimethyl formamide, dimethyl acetamide, acetonitrile, methanol, ethanol, isopropanol, butanol, acetone, methyl isobutyl ketone, methyl ethyl ketone, ethyl acetate, isopropyl acetate, butyl acetate, diethyl ether, diisopropyl ether, methylene dichloride. In particular, methanol may be used.

In general, the reduction may be done with suitable reducing agent selected from lithium aluminium hydride (LiAlH4), Raney Nickel, Nascent (atomic) hydrogen; sodium amalgam, sodium borohydride, Palladium carbon, Platinum carbon, Hydrazine, Zinc-mercury amalgam, diisobutylaluminum hydride, Lindlar catalyst. In particular, palladium catalyst may be used.

The embodiment of the process includes resolution of compound (M). The resolution may be performed in one or more of suitable solvent selected from the group consisting toluene, xylene, ethylbenzene dimethyl formamide, dimethyl acetamide, acetonitrile, methanol, ethanol, isopropanol, butanol, acetone, methyl isobutyl ketone, methyl ethyl ketone, ethyl acetate, isopropyl acetate, butyl acetate, diethyl ether, diisopropyl ether. In particular, ethanol may be used.

In general, the salt of Formula (N) may be treated with suitable acid to obtain compound of Formula (I). The suitable acid may be selected from hydrochloric acid, sulfuric acid, acetic acid, trifluoro acetic acid, nitric acid, phosphoric acid and the like. In particular, hydrochloric acid may be used.

In another general aspect, there is provided a crystalline form of (3aR,7aR)-4'-(benzo[d]isothiazol-3-yl)octahydrospiro[isoindole-2,1'-piperazin]-1'-ium mesylate of Formula (G).

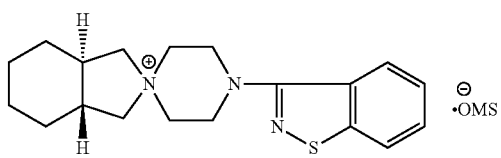

(G)

In another general aspect, there is provided a crystalline form of (3aR,7aR)-4'-(benzo[d]isothiazol-3-yl)octahydrospiro[isoindole-2,1'-piperazin]-1'-ium mesylate of Formula (G) characterized by X-ray powder diffraction (FIG. 5) and DSC (FIG. 6)

In general, the crystalline form of (3aR,7aR)-4'-(benzo[d]isothiazol-3-yl)octahydrospiro[isoindole-2,1'-piperazin]-1'-ium mesylate of Formula (G) is characterized by X-ray powder diffraction having characteristic peaks at about 8.9°, 11.1°, 12.3°, 15.1°, 15.8°, 18.9°, 19.5°, 20.6°, 20.9°, 22.5° and 25.5°±0.2 degrees 2θ.

The crystalline form of (3aR,7aR)-4'-(benzo[d]isothiazol-3-yl)octahydrospiro[isoindole-2,1'-piperazin]-1'-ium mesylate of Formula (G) is further characterized by X-ray powder diffraction having characteristic peaks at about 7.6°, 8.2°, 14.7°, 16.9°, 18.3°, 19.8°, 20.1°, 21.3°, 22.2°, 22.9°, 23.8°, 25.0°, 26.9°, 29.4°, 30.2° and 31.5°±0.2 degrees 2θ.

The crystalline form of (3aR,7aR)-4'-(benzo[d]isothiazol-3-yl)octahydrospiro[isoindole-2,1'-piperazin]-1'-ium mesylate of Formula (G) is further characterized by differential scanning calorimetry (DSC) having peak at about 230° C.

In another general aspect, there is provided a process for preparing crystalline form of (3 aR,7aR)-4'-(benzo[d]isothiazol-3-yl)octahydrospiro[isoindole-2,1'-piperazin]-1'-ium mesylate of Formula (G),

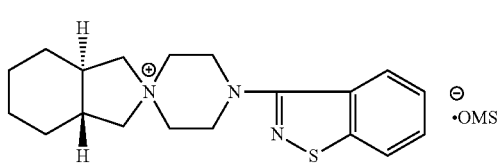

(G)

the process comprising reacting (1R,2R)-cyclohexane-1,2-diylbis(methylene)dimethanesulfonate of Formula (B)

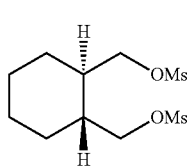
(B)

with 3-(piperazin-1-yl)benzo[d]isothiazole of Formula (F)

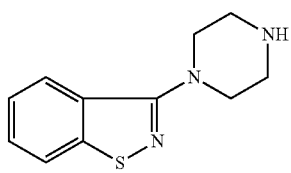
(F)

in presence of base and a phase transfer catalyst in one or more of suitable solvent to obtain (3aR,7aR)-4'-(benzo[d]isothiazol-3-yl)octahydrospiro[isoindole-2,1'-piperazin]-1'-ium mesylate of Formula (G) and obtaining crystalline (3aR,7aR)-4'-(benzo[d]isothiazol-3-yl)octahydrospiro-[isoindole-2,1'-piperazin]-1'-ium mesylate by removal of solvent.

In general, the suitable solvent comprises one or more of hydrocarbons, nitriles, amides, alcohol, ketones, ester and the like. In particular, the suitable solvent comprises toluene, xylene, ethylbenzene dimethyl formamide, dimethyl acetamide, acetonitrile, methanol, ethanol, isopropanol, butanol, acetone, methyl isobutyl ketone, methyl ethyl ketone, ethyl acetate, isopropyl acetate, butyl acetate. In particular, acetone may be used.

The embodiments of the process include reaction in presence of base and a phase transfer catalyst. The suitable base may be selected from the group consisting of inorganic base such as hydroxides, carbonates and bicarbonates of alkali or alkaline earth metals and organic base. In particular, the suitable base comprises of sodium hydroxide, potassium hydroxide, lithium hydroxide, sodium carbonate, potassium carbonate, sodium bicarbonate, potassium bicarbonate and the like and triethyl amine (TEA), diisopropylethylamine (DIPEA), diisopropylamine (DIPA). In particular, sodium carbonate may be used.

In general, the phase transfer catalyst (PTC) comprises of benzyltrimethylammonium chloride, hexadecyltributyl phosphonium bromide, tetrabutyl ammonium hydrogen sulphate, tetrabutylammonium bromide, methyltrioctyl ammonium chloride, crown ethers, polyethylene glycols. In particular, tetrabutyl ammonium hydrogen sulphate may be used.

According to further embodiments of the process, the crystalline form of (3 aR,7aR)-4'-(benzo[d]isothiazol-3-yl)octahydrospiro[isoindole-2,1'-piperazin]-1'-ium mesylate of Formula (G) may be obtained by crystallization or recrystallization of obtained compound (G) during reaction in one or more of suitable organic solvent followed by removal of solvent. The suitable solvent comprises one or more of methanol, ethanol, isopropanol, butanol, dimethyl formamide, dimethyl acetamide, acetonitrile, acetone, methyl isobutyl ketone, methyl ethyl ketone, ethyl acetate, isopropyl acetate, butyl acetate, toluene, xylene, ethylbenzene and the like. In particular, ethyl acetate or acetone may be used.

In another general aspect, there is provided a crystalline form of lurasidone free base of Formula (H)

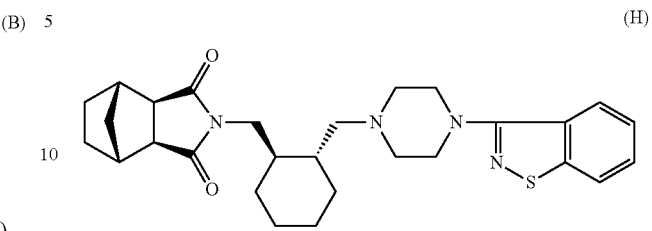
(H)

In another general aspect, there is provided a crystalline form of lurasidone free base of Formula (H) characterized by X-ray powder diffraction (FIG. 3) and DSC (FIG. 4)

In general, the crystalline form of lurasidone free base of Formula (H) is characterized by X-ray powder diffraction having characteristic peaks at about 11.1°, 13.9°, 15.0°, 15.4°, 16.2°, 16.5°, 17.9°, 19.1°, 19.9°, 20.8°, 22.2° and 26.0° 10.2 degrees 2θ.

The crystalline form of lurasidone free base of Formula (H) is further characterized by X-ray powder diffraction having characteristic peaks at about 8.0°, 9.6°, 11.5°, 19.4°, 20.1°, 23.3°, 24.0°, 24.6°, 25.3°, 26.8°, 29.9° and 33.8°±0.2 degrees 2θ.

The crystalline form of lurasidone free base of Formula (H) is characterized by differential scanning calorimetry (DSC) having peak at about 151° C.

In another general aspect, there is provided a process for preparing crystalline form of lurasidone free base of Formula (H),

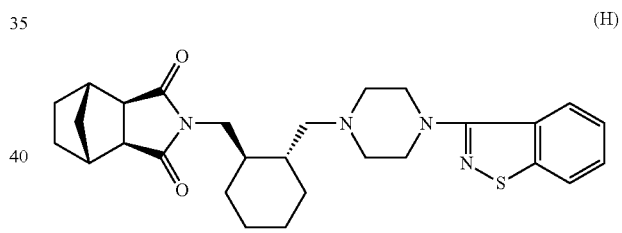
(H)

the process comprising reacting (3aR,7aR)-4'-(benzo[d]isothiazol-3-yl)octahydrospiro[isoindole-2,1'-piperazin]-1'-ium mesylate of Formula (G)

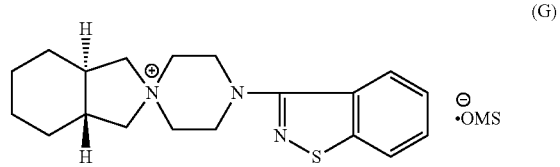 [SMILES: c1ccc2c(N3CC[N+]4(CC3)C[C@@H]3CCCC[C@H]3C4)nsc2c1]
(G)

with bicyclo[2.2.1]heptane-2-exo-3exo-dicarboximide of Formula (E)

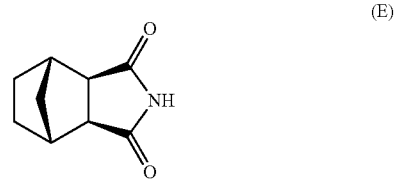
(E)

in presence of base and phase transfer catalyst in one or more of suitable organic solvent to obtain lurasidone free base and obtaining crystalline form of lurasidone free base of Formula (H) by removal of solvent.

In general, the suitable organic solvent comprises one or more of hydrocarbons, nitriles, amides, alcohol, ketones, ester and the like. In particular, the suitable organic solvent comprises one or more of toluene, xylene, ethylbenzene, acetonitrile, ethyl acetate, isopropyl acetate, butyl acetate, acetone, ethyl methyl ketone, methyl isobutyl ketone and the like. In particular, xylene may be used.

The suitable base may be selected from the group consisting of inorganic base such as hydroxides, carbonates and bicarbonates of alkali or alkaline earth metals and organic base. In particular, the suitable base comprises of sodium hydroxide, potassium hydroxide, lithium hydroxide, sodium carbonate, potassium carbonate, sodium bicarbonate, potassium bicarbonate and the like and triethyl amine (TEA), diisopropylethylamine (DIPEA), diisopropylamine (DIPA). In particular, potassium carbonate may be used.

In general, the phase transfer catalyst (PTC) comprises of benzyltrimethylammonium chloride, hexadecyltributyl phosphonium bromide, tetrabutyl ammonium hydrogen sulphate, tetrabutylammonium bromide, methyltrioctyl ammonium chloride, crown ethers like dibenzo-18-crown-ether, polyethylene glycols. In particular, dibenzo-18-crown-ether may be used.

According to further embodiments of the process, the crystalline form of lurasidone free base of Formula (H) may be obtained by crystallization or recrystallization of obtained compound (H) during reaction in one or more of suitable organic solvent followed by removal of solvent. The suitable organic solvent comprises of methanol, ethanol, isopropanol, butanol, dimethyl formamide, dimethyl acetamide, acetonitrile, acetone, methyl isobutyl ketone, methyl ethyl ketone, ethyl acetate, isopropyl acetate, butyl acetate and the like. In particular, isopropanol may be used.

In another general aspect, there is provided a process for preparation of crystalline form of lurasidone hydrochloride of Formula (1),

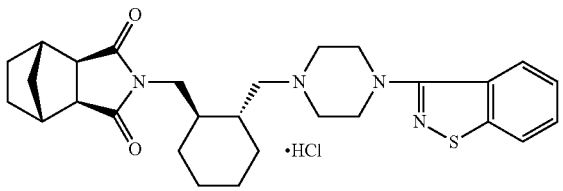

the process comprising:
(a) reacting (3aR,7aR)-4'-(benzo[d]isothiazol-3-yl)octahydrospiro[isoindole-2,1'-piperazin]-1'-ium mesylate of Formula (G) and bicyclo[2.2.1]heptane-2-exo-3-exo-dicarboximide of Formula (E) in presence of base and a phase transfer catalyst in one or more of suitable organic solvent to obtain lurasidone free base of Formula (H);
(b) reacting lurasidone free base of Formula (H) with hydrochloric acid source in one or more of suitable solvent to obtain lurasidone hydrochloride; and
(c) obtaining crystalline form of lurasidone hydrochloride of Formula (1).

In another general aspect, there is provided a process for preparation of crystalline lurasidone hydrochloride of Formula (1),

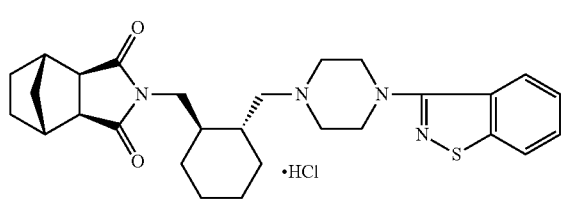

the process comprising:
(a) reducing (1R,2R)-(−)-trans-cyclohexane-1,2-dicarboxylic acid with a suitable reducing agent in one or more of suitable organic solvent to obtain (1R,2R)-(−)-trans-cyclohexane-1,2-diyldimethanol of Formula (A);
(b) reacting (1R,2R)-(−)-trans-cyclohexane-1,2-diyldimethanol of Formula (A) with methanesulfonyl chloride in presence of base in one or more of suitable organic solvent to obtain (1R,2R)-(−)-trans-cyclohexane-1,2-diylbis(methylene)dimethanesulfonate of Formula (B);
(c) reacting (1R,2R)-(−)-trans-cyclohexane-1,2-diylbis(methylene)dimethanesulfonate of Formula (B) and 3-(piperazin-1-yl)benzo[d]isothiazole of Formula (F) in presence of base and a phase transfer catalyst in one or more of suitable organic solvent to obtain crystalline form of (3aR, 7aR)-4'-(benzo[d]isothiazol-3-yl)octahydrospiro[isoindole-2,1'-piperazin]-1'-ium mesylate of Formula (G);
(d) reacting crystalline form of (3aR,7aR)-4'-(benzo[d]isothiazol-3-yl)octahydrospiro[isoindole-2,1'-piperazin]-1'-ium mesylate of Formula (G) with (3aS,4R,7S,7aR)-hexahydro-4,7-methano-1H-isoindole-1,3-(2H)-dione of Formula (E) in presence of base and a phase transfer catalyst in one or more of suitable organic solvent to obtain crystalline form of lurasidone free base of Formula (H);
(e) reacting crystalline form of lurasidone free base of Formula (H) with hydrochloric acid source in one or more of suitable organic solvent to obtain lurasidone hydrochloride of Formula (1); and
(f) obtaining crystalline form of lurasidone hydrochloride of Formula (1) by removal of solvent.

In general, the suitable organic solvent for step (a) comprises one or more of $C_1$-$C_5$ alcohols, esters, ethers, water or a mixture thereof. In particular, methanol, ethanol, isopropanol, butanol, ethyl acetate, isopropyl acetate, butyl acetate, diethyl ether, diisopropylether, methyltertbutyl ether, tetrahydrofuran, 2-methyltetrahydforuan, 1,4-dioxane and the like. In particular, tetrahydrofuran may be used.

The reducing agent for step (a) may be selected from the group consisting of sodium borohydide, lithium aluminium hydride, Vitride and the like. In particular, lithium aluminium hydride may be used.

The obtained compound (A) in step (a) may be reacted methane sulfonyl chloride in presence of base in suitable organic solvent. The suitable organic solvent comprises one or more of methanol, ethanol, isopropanol, butanol, ethyl acetate, isopropyl acetate, butyl acetate, diethyl ether, diisopropyl ether, methyl tertbutyl ether, tetrahydrofuran, 1,4-dioxane, methylene dichloride, ethylene dichloride, chloroform, chlorobenzene, water or a mixture thereof. In particular, methylene dichloride may be used.

The suitable base comprises of sodium hydroxide, potassium hydroxide, lithium hydroxide, sodium carbonate, potassium carbonate, sodium bicarbonate, potassium bicarbonate and the like and triethyl amine (TEA), diisopropylethylamine (DIPEA), diisopropylamine (DIPA). In particular, triethyl amine (TEA) may be used.

In general, reaction of (1R,2R)-(−)-trans-cyclohexane-1,2-diylbis(methylene)dimethanesulfonate of Formula (B) and 3-(piperazin-1-yl)benzo[d]isothiazole of Formula (F) is done in suitable solvent comprises one or more of hydrocarbons, nitrites, amides, alcohol, ketones, ester and the like. In particular, the suitable solvent comprises toluene, xylene, ethylbenzene dimethyl formamide, dimethyl acetamide, acetonitrile, methanol, ethanol, isopropanol, butanol, acetone, methyl isobutyl ketone, methyl ethyl ketone, ethyl acetate, isopropyl acetate, butyl acetate. In particular, acetone may be used.

The embodiments of the process include reaction in presence of base and a phase transfer catalyst. The suitable base in step (c) may be selected from the group consisting of inorganic base such as hydroxides, carbonates and bicarbonates of alkali or alkaline earth metals and organic base. In particular, the suitable base comprises of sodium hydroxide, potassium hydroxide, lithium hydroxide, sodium carbonate, potassium carbonate, sodium bicarbonate, potassium bicarbonate and the like and triethyl amine (TEA), diisopropylethylamine (DIPEA), diisopropylamine (DIPA). In particular, sodium carbonate may be used.

In general, the phase transfer catalyst (PTC) comprises of benzyltrimethylammonium chloride, hexadecyltributyl phosphonium bromide, tetrabutyl ammonium hydrogen sulphate, tetrabutylammonium bromide, methyltrioctyl ammonium chloride, crown ethers, polyethylene glycols. In particular, tetrabutyl ammonium hydrogen sulphate may be used.

According to further embodiments of the process, the crystalline form of (3aR,7aR)-4'-(benzo[d]isothiazol-3-yl)octahydrospiro[isoindole-2,1'-piperazin]-1'-ium mesylate of Formula (G) may be obtained by crystallization or recrystallization of obtained compound (G) during reaction in one or more of suitable organic solvent followed by removal of solvent. The suitable solvent comprises one or more of methanol, ethanol, isopropanol, butanol, dimethyl formamide, dimethyl acetamide, acetonitrile, acetone, methyl isobutyl ketone, methyl ethyl ketone, ethyl acetate, isopropyl acetate, butyl acetate, toluene, xylene, ethylbenzene and the like. In particular, ethyl acetate or acetone may be used.

In general, the crystalline compound (G) is reacted (3aS,4R,7S,7aR)-hexahydro-4,7-methano-1H-isoindole-1,3-(2H)-dione of Formula (E) in suitable organic solvent comprises one or more of hydrocarbons, nitriles, amides, alcohol, ketones, ester and the like. In particular, the suitable solvent comprises of toluene, xylene, ethylbenzene, acetonitrile, ethyl acetate, isopropyl acetate, butyl acetate, acetone, ethyl methyl ketone, methyl isobutyl ketone and the like. In particular, xylene may be used.

The embodiments of the process include reaction in presence of base and a phase transfer catalyst. The suitable base in step may be selected from the group consisting of inorganic base such as hydroxides, carbonates and bicarbonates of alkali or alkaline earth metals and organic base. In particular, the suitable base comprises of sodium hydroxide, potassium hydroxide, lithium hydroxide, sodium carbonate, potassium carbonate, sodium bicarbonate, potassium bicarbonate and the like and triethyl amine (TEA), diisopropylethylamine (DIPEA), diisopropylamine (DIPA). In particular, potassium carbonate may be used.

In general, the phase transfer catalyst (PTC) comprises of benzyltrimethylammonium chloride, hexadecyltributyl phosphonium bromide, tetrabutyl ammonium hydrogen sulphate, tetrabutylammonium bromide, methyltrioctyl ammonium chloride, crown ethers like dibenzo-18-crown-ether, polyethylene glycols. In particular, dibenzo-18-crown-ether may be used.

According to further embodiments of the process, the crystalline form of lurasidone free base of Formula (H) may be obtained by crystallization or recrystallization of obtained compound (H) during reaction in one or more of suitable organic solvent followed by removal of solvent. The suitable solvent comprises methanol, ethanol, isopropanol, butanol, dimethyl formamide, dimethyl acetamide, acetonitrile, acetone, methyl isobutyl ketone, methyl ethyl ketone, ethyl acetate, isopropyl acetate, butyl acetate and the like. In particular, isopropanol may be used.

The crystalline lurasidone free base may be converted to its hydrochloride salt by treating with hydrochloric acid source. The hydrochloric acid source comprises hydrochloric acid, aqueous hydrochloric acid, hydrochloric acid gas, isopropanolic hydrochloride, ethyl acetate hydrochloric acid, acetone hydrochloric acid etc. In particular, isopropanolic hydrochloride acid may be used.

The suitable solvent for step (e) comprises one or more of hydrocarbons, nitriles, amides, alcohol, ketones, ester and the like. In particular, the suitable solvent comprises of toluene, xylene, ethylbenzene dimethyl formamide, dimethyl acetamide, acetonitrile, methanol, ethanol, isopropanol, butanol, acetone, methyl isobutyl ketone, methyl ethyl ketone, ethyl acetate, isopropyl acetate, butyl acetate. In particular, methanol may be used.

The crystalline form of lurasidone hydrochloride represented by Formula (1) prepared by the process of the present invention may be characterized by X-ray powder diffraction (FIG. 1) and DSC (FIG. 2)

In general, the crystalline form of lurasidone hydrochloride of Formula (1) is characterized by X-ray powder diffraction having characteristic peaks at about 11.4°, 13.9°, 15.1°, 15.5°, 16.4°, 17.1°, 17.4°, 19.5°, 20.8°, 21.9°, and 27.4°±0.2 degrees 2θ.

The crystalline form of lurasidone hydrochloride of Formula (1) is further characterized by X-ray powder diffraction having characteristic peaks at about 8.5°, 14.4°, 17.9°, 18.7°, 21.2°, 23.0°, 23.5°, 24.2°, 25.3°, 27.9°, 28.3°, 29.4°, 30.2°, 31.6° and 33.2°±0.2 degrees 2θ.

The crystalline form of lurasidone hydrochloride of Formula (1) is characterized by differential scanning calorimetry (DSC) having peak at about 282° C.

In another general aspect, there is provided crystalline form of lurasidone hydrochloride of Formula (1) substantially free of impurities and having purity greater than about 99%, particularly greater than about 99.5% as measured by HPLC.

In another general aspect, there is provided a process for preparing (1R,2R)-cyclohexane-1,2-diylbis(methylene) dimethanesulfonate of Formula (B)

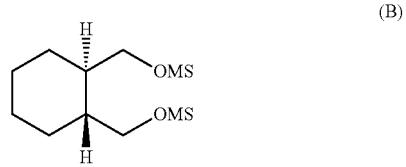

(B)

the process comprising:

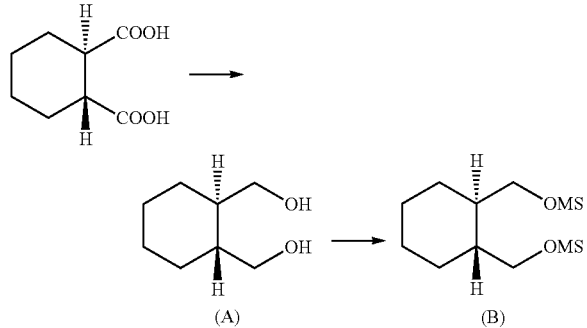

(a) reducing (1R,2R)-(−)-trans-cyclohexane-1,2-dicarboxylic acid with a suitable reducing agent in suitable organic solvent to obtain (1R,2R)-cyclohexane-1,2-diyldimethanol of Formula (A);
(b) reacting (1R,2R)-(−)-trans-cyclohexane-1,2-diyldimethanol of Formula (A) with methanesulfonyl chloride in presence of a base in suitable organic solvent; and
(c) obtaining (1R,2R)-(−)-trans-cyclohexane-1,2-diylbis(methylene)dimethanesulfonate of Formula (B).

In general, the suitable organic solvent for step (a) comprises one or more of $C_1$-$C_5$ alcohols, esters, ethers, water or a mixture thereof. In particular, methanol, ethanol, isopropanol, butanol, ethyl acetate, isopropyl acetate, butyl acetate, diethyl ether, diisopropylether, methyltertbutyl ether, tetrahydrofuran, 2-methyltetrahydforuan, 1,4-dioxane and the like. In particular, tetrahydrofuran may be used.

The reducing agent for step (a) may be selected from the group consisting of sodium borohydide, lithium aluminium hydride, Vitride and the like. In particular, lithium aluminium hydride may be used.

The obtained compound (A) in step (a) may be reacted methane sulfonyl chloride in presence of base in suitable organic solvent. The suitable organic solvent comprises one or more of methanol, ethanol, isopropanol, butanol, ethyl acetate, isopropyl acetate, butyl acetate, diethyl ether, diisopropyl ether, methyl tertbutyl ether, tetrahydrofuran, 1,4-dioxane, methylene dichloride, ethylene dichloride, chloroform, chlorobenzene, water or a mixture thereof. In particular, methylene dichloride may be used.

The suitable base comprises of sodium hydroxide, potassium hydroxide, lithium hydroxide, sodium carbonate, potassium carbonate, sodium bicarbonate, potassium bicarbonate and the like and triethyl amine (TEA), diisopropylethylamine (DIPEA), diisopropylamine (DIPA). In particular, triethyl amine (TEA) may be used.

The suitable solvent in step (b) for obtaining (1R,2R)-(−)-trans-cyclohexane-1,2-diylbis(methylene)dimethanesulfonate of Formula (B) comprises of water, hydrocarbons, nitriles, amides, alcohol, halogenated solvents, ketones, esters, ethers and the like. In particular, the suitable solvent comprises toluene, xylene, ethylbenzene dimethyl formamide, dimethyl acetamide, acetonitrile, $C_1$-$C_4$ straight chain or branched alcohols, acetone, methyl isobutyl ketone, methyl ethyl ketone, ethyl acetate, isopropyl acetate, butyl acetate, diethyl ether, diisopropyl ether. In particular, diethyl ether and water.

In another general aspect, there is provided a process for preparing (3aS,4R,7S,7aR)-hexahydro-4,7-methano-1H-isoindole-1,3-(2H)-dione of Formula (E)

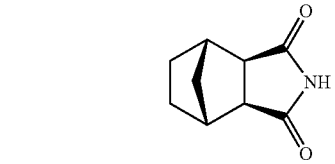

the process comprising:

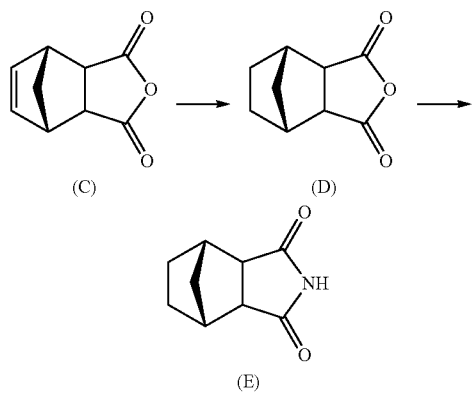

(a) reducing bicyclo[2.2.1]hept-5-ene-2-exo-3-exo-dicarboxylic acid anhydride of Formula (C) a suitable reducing agent in a suitable solvent to obtain bicyclo[2.2.1]heptane-2-exo-3-exo-dicarboxylic acid anhydride of Formula (D); and
(b) reacting bicyclo[2.2.1]heptane-2-exo-3-exo-dicarboxylic acid anhydride of Formula (D) in presence of a base in suitable organic solvent to obtain (3aS,4R,7S,7aR)-hexahydro-4,7-methano-1H-isoindole-1,3-(2H)-dione of Formula (E).

The suitable solvent for step (a) comprises hydrocarbons, nitriles, amides, alcohols, ketones, esters, ethers and the like. In particular, the suitable solvent comprises toluene, xylene, ethylbenzene dimethyl formamide, dimethyl acetamide, acetonitrile, $C_1$-$C_4$ straight chain or branched alcohols, acetone, methyl isobutyl ketone, methyl ethyl ketone, ethyl acetate, isopropyl acetate, butyl acetate, tetrahydrofuran (THF), diethyl ether preferably tetrahydrofuran (THF).

The reducing agent for step (a) is selected from $SnCl_2$, Raney-Ni, Pd/C etc. In particular, Pd/C may be used.

The suitable solvent for step (b) comprises one or more of hydrocarbons, nitriles, amides, alcohols, ketones, esters, ethers and the like. In particular, the suitable solvent comprises toluene, xylene, ethylbenzene dimethyl formamide, dimethyl acetamide, acetonitrile, $C_1$-$C_4$ straight chain or branched alcohols, acetone, methyl isobutyl ketone, methyl ethyl ketone, ethyl acetate, isopropyl acetate, butyl acetate, tetrahydrofuran (THF), diethyl ether. In particular, tetrahydrofuran (THF) may be used.

The suitable base for step (b) is liquor ammonia.

The suitable solvent in step (b) for obtaining bicyclo[2.2.1]heptane-2-exo-3-exo-dicarboximide of Formula (E) is selected from the group consisting of water, hydrocarbons, nitriles, amides, alcohol, halogenated solvents, ketones, esters, ethers and the like. In particular, the suitable solvent comprises toluene, xylene, ethylbenzene dimethyl formamide, dimethyl acetamide, acetonitrile, $C_1$-$C_4$ straight chain or branched alcohols, acetone, methyl isobutyl ketone, methyl ethyl ketone, ethyl acetate, isopropyl acetate, butyl acetate, diethyl ether, diisopropyl ether. In particular, toluene may be used.

In another general aspect, there is provided Lurasidone hydrochloride of Formula (1) having a total purity of greater than about 99%, specifically greater than about 99.5%, more specifically greater than about 99.9%, and most specifically greater than about 99.98% as measured by HPLC.

In another general aspect, there is provided particle size of lurasidone hydrochloride of Formula (1).

The crystalline lurasidone hydrochloride of Formula (1) of present invention having an average particle size in the range of 5 to 300 microns, particularly 20 to 150 microns, more particularly 50 to 100 microns. The term "average particle size" or "particle size" as used herein refers to the volume mean diameter of particles.

In another general aspect, there is provided lurasidone hydrochloride having particle size in terms of $d_{90}$ is less than about 100 microns. Lurasidone hydrochloride can be further micronized to obtain particles with $d_{90}$ less than about 60 microns, more particularly $d_{90}$ less than about 40 microns, and most particularly $d_{90}$ less than about 30 microns. As used herein $d_{90}$ less than about x means that at least 90% by volume of the particles have a particle size below x.

In another general aspect, there is provided microcrystalline lurasidone hydrochloride having particle size in terms of $d_{90}$ is less than about 10 microns.

The particle size can be determined by laser light scattering for instance using a Malvern Mastersizer Apparatus MS 2000 equipped with a Hydro S dispersion unit using purified water as the dilution medium. Micronized Lurasidone hydrochloride can be obtained for instance by single or multi-stage micronization in the dry state using dry mills, such as cutting mills, pin/cage mills, hammer mills, jet mills, fluidized bed jet mills, ball mills and roller mills.

In another general aspect, there is provided a pharmaceutical composition comprising therapeutically effective amount of cyrstalline lurasidone hydrochloride of Formula (1) and one or more of pharmaceutically acceptable carriers, excipients or diluents.

The pharmaceutical compositions may be in a solid or liquid dosage form. Exemplary solid dosage forms include tablets, capsules, sachets, lozenges, powders, pills, pellets, or granules. The solid dosage form may be, for example, a immediate release dosage form, a fast melt dosage form, orally disintegrating dosage form, modified release dosage form, lyophilized dosage form, delayed release dosage form, extended release dosage form, prolonged release dosage form, pulsatile dosage form, mixed immediate and modified release dosage form, or a combination thereof. Solid dosage forms are preferred. More preferably, the solid dosage form is an immediate release dosage form offering advantages regarding the bioavailability of the active compound.

Pharmaceutical dosage forms comprising lurasidone hydrochloride may be prepared by a process comprising the steps of mixing lurasidone hydrochloride according to the present invention with at least one pharmaceutically acceptable excipient and forming the mixture into a pharmaceutical dosage form. Lurasidone hydrochloride (1) and the one or more excipients can be mixed in the presence or in the absence of solvent.

In another general aspect, the process for preparation of lurasidone hydrochloride of Formula (1) as is shown in below Scheme (1) and (2):

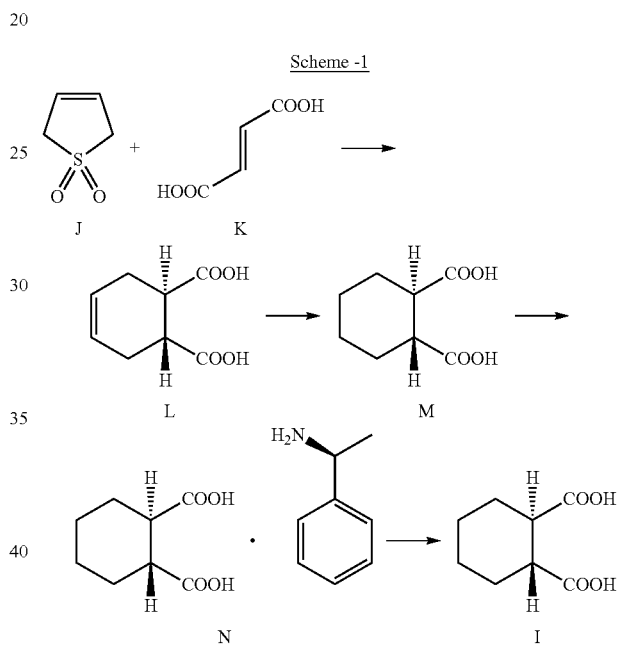

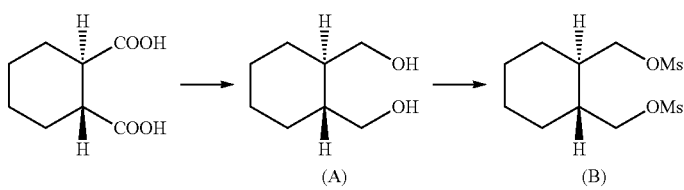

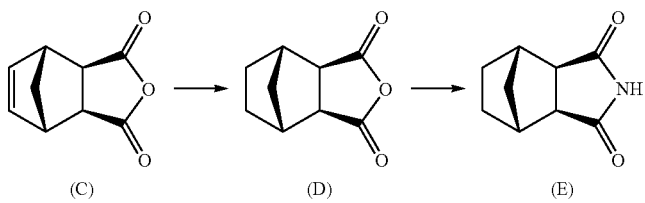

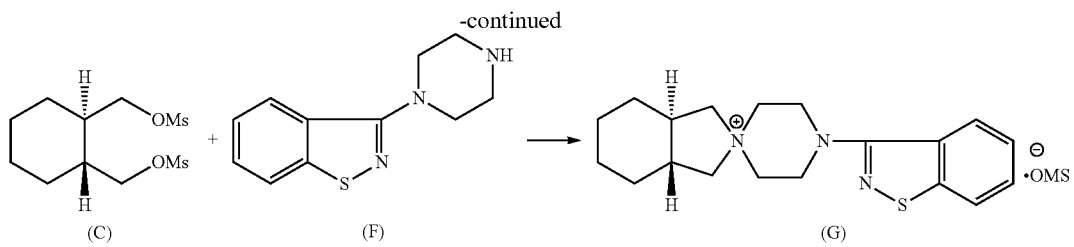

(C)     (F)     (G)

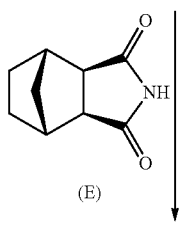

(E)

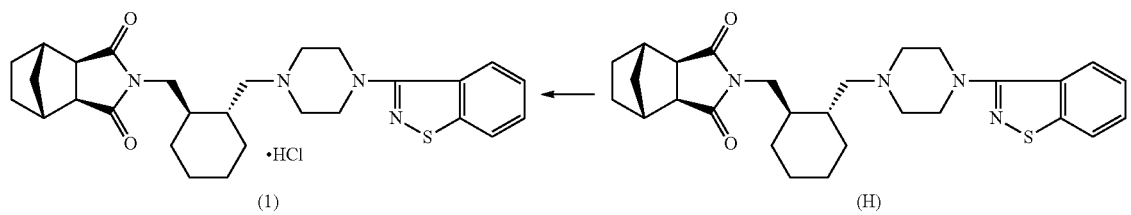

(1)     (H)

The present invention is further illustrated by the following example which is provided merely to be exemplary of the invention and do not limit the scope of the invention. Certain modification and equivalents will be apparent to those skilled in the art and are intended to be included within the scope of the present invention.

Example-1

Preparation of (1R,2R)-(−)-trans-cyclohexene-1,2-dicarboxylic acid (L)

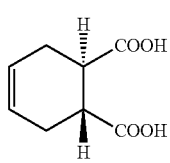

(L)

100 g fumaric acid and 153.2 g butadiene sulfolane along with 1000 mL of acetic acid were charged in a reactor and heated upto 100° C.-105° C. The reaction mixture was maintained until completion and subsequently cooled. The reaction mixture was charcoalized and filtered. The filtrate was distilled under vacuum to remove acetic acid. The residue was treated with 800 mL acetone and charcoalized. The reaction mixture was stirred for 30 min and filtered. The wet-cake was washed with acetone. The filtrate was distilled under vacuum to remove acetone and residue was treated with 100 mL water. The reaction mixture was cooled to 5-10° C. and precipitated product was filtered. The wet-cake was washed with water.

The obtained title compound (1R,2R)-(−)-trans-cyclohexene-1,2-dicarboxylic acid (L) was recrystallized in water. Purity>99.5% by HPLC.

Example-2

Preparation of (1R,2R)-(−)-trans-cyclohexane-1,2-dicarboxylic acid (racemic) (M)

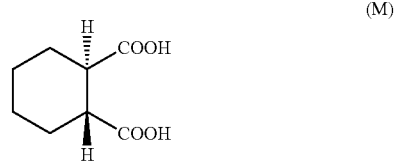 [SMILES: O=C(O)[C@@H]1CCCC[C@H]1C(=O)O]

(M)

100 g (1R,2R)-(−)-trans-cyclohexene-1,2-dicarboxylic acid (L) and 1500 mL of methanol was charged along with 5 g of palladium catalyst into a reactor with hydrogen purging facility. Hydrogen purging was carried out at 30-35° C. until the completion of the reaction. The reaction mass was filtered and washed with methanol. The filtrate was distilled under vacuum to remove methanol. The residue was treated with 200 mL ethyl acetate and heated at 60° C. with stirring. The reaction mixture was cooled, and stirred for 1 hour. The precipitated product was filtered and washed with ethyl acetate to obtain (1R,2R)-(−)-trans-cyclohexane-1,2-dicarboxylic acid (racemic) (M).

Example-3

Preparation of R-(α)-methyl benzyl amine salt of (1R,2R)-(−)-trans-cyclohexane-1,2-dicarboxylic acid (N)

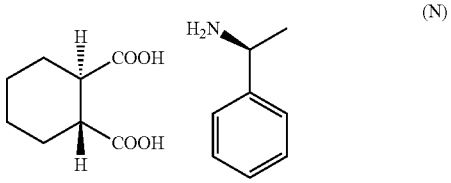

100 g (1R,2R)-(−)-trans-cyclohexane-1,2-dicarboxylic acid (racemic) (M) and 1600 ml of ethanol were charged in round bottom flask, heated upto 75° C. and 70 g of R-(+)-alpha methyl benzylamine was added. The reaction mixture was cooled to 35° C. and stirred for 30 hours. The reaction mixture was filtered and washed with ethanol. The product obtained was recrystallized using 1500 ml of ethanol to afford R-(a)-methyl benzylamine salt of (1R,2R)-(−)-trans-cyclohexane-1,2-dicarboxylic acid (N).

Example-4

Preparation of pure (1R,2R)-(−)-trans-cyclohexane-1,2-dicarboxylic acid (I)

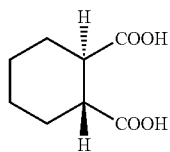

60 g of R-(α)-methyl benzylamine salt of (1R,2R)-(−)-trans-cyclohexane-1,2-dicarboxylic acid (N), 125 mL water and 1500 mL ethyl acetate were charged into a reactor, to which 25 ml of Conc. HCl was added while stirring for one hour. The reaction mixture was settled and ethyl acetate layer was extracted. The aqueous layer was extracted with 300 mL of ethyl acetate and washed with aq. sodium chloride solution and again extracted, filtered and ethyl acetate was distilled under vacuum. The residue was treated with 200 mL of cyclohexane stirred for 15 min and filtered to obtain pure (1R,2R)-(−)-trans-cyclohexane-1,2-dicarboxylic acid (I). Chiral purity>99.9%, HPLC Purity>99.5%.

Example-5

Preparation of (1R,2R)-(−)-trans-cyclohexane-1,2-diyldimethanol of Formula (A)

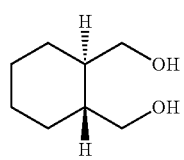

60 g Lithium aluminum hydride and 470 mL tetrahydrofuran were added to a round bottom flask at 25° C. and stirred for 10 min to obtain reaction mixture. The reaction mixture was heated to 65° C. and 100 g (1R,2R)-cyclohexane-1,2-dicarboxylic acid solution in 1200 mL THF was added. The reaction mixture was stirred for 3 hours and cooled to 5° C. 500 mL aqueous tetrahydrofuran solution was added and stirred for 30 min. The reaction mixture was filtered and washed with 200 mL tetrahydrofuran. The salt was treated with 670 mL tetrahydrofuran at 65° C. and cooled. The reaction mixture was filtered. The filtrate was distilled to remove tetrahydrofuran to obtain thick oily residue. The residue was treated with cyclohexane (600 mL) and stirred for 1 hour at 15° C. The product obtained was filtered and washed with cyclohexane to obtain (1R,2R)-(−)-trans-cyclohexane-1,2-diyldimethanol of Formula (A).

Example-6

Preparation of (1R,2R)-(−)-trans-cyclohexane-1,2-diylbis(methylene)dimethane-sulfonate of Formula (B)

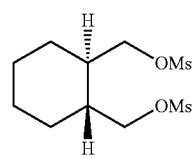

100 g (1R,2R)-(−)-trans-cyclohexane-1,2-diyldimethanol of Formula (A) and 1400 mL of methylene dichloride were added to RBF at 25 to 35° C. under nitrogen atmosphere and stirred for 15 minutes followed by addition of 210 g of triethylamine at 0° C. The reaction mixture was stirred for 10 minutes and cooled to −5° C. followed by addition of 200 g of methanesulfonyl chloride. The temperature was raised to 25 to 30° C. The reaction mixture was stirred for 3 hours and settled to separate the organic layer. The separated organic layer was washed with 1000 mL water and distilled under vacuum to obtain residue. The residue was treated with 800 mL diethyl ether and filtered to obtain the title compound as (1R,2R)-(−)-trans-cyclohexane-1,2-diylbis(methylene)dimethanesulfonate of Formula (B).

Example-7

Preparation of bicyclo[2.2.1]hept-5-ene-2-exo-3-exo-dicarboxylic acid anhydride (C)

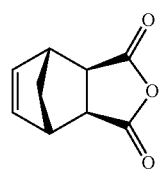

250 ml dicyclopentadiene was charged in a round bottom flask and distilled at vapour temp. of 35-50° C. to distill out 200-215 ml of cyclopentadiene which was stored in freezer.

In another round bottom flask 100 g maleic anhydried was heated at 200° C. to which the stored 88 g cyclopentadiene was slowly added. The reaction mixture was stirred for one hour at 200° C. The reaction mass was cooled naturally at 90° C., 140 mL benzene was added and stirred for 30 min at 80° C. The reaction mixture after completion of the reaction as monitored by TLC, was allowed to cool naturally at room temperature and stirred for 4-5 hours, filtered, washed with benzene. The dried material was recrystallized thrice with benzene to afford bicyclo[2.2.1]hept-5-ene-2-exo-3-exo-dicarboxylic acid anhydride (C).

Example-8

Preparation of bicyclo[2.2.1]heptane-2-exo-3-exo-dicarboxylic acid anhydride of Formula (D)

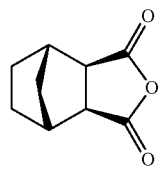

(D)

100 g bicyclo[2.2.1]hept-5-ene-2-exo-3-exo-dicarboxylic acid anhydride of Formula (C) and 15 g Pd—C were added to 5 L autoclave. The assembly was flushed two times with $N_2$ gas at 5 Kg pressure and with $H_2$ gas at 5 Kg pressure at 25° C. to 35° C. The pressure of $H_2$ gas was set at 5 Kg and reaction was stirred for 2 hours at 5 Kg pressure of $H_2$ gas at 25° C. to 35° C. and $H_2$ gas was released and the assembly was flushed with $N_2$ gas at 5 Kg pressure. The product was treated with 200 mL hexane and stirred for 1 hour and finally washed with chilled 200 mL hexane to afford the title compound as bicyclo[2.2.1]heptane-2-exo-3-exo-dicarboxylic acid anhydride of Formula (D).

Example-9

Preparation of (3aS,4R,7S,7aR)-hexahydro-4,7-methano-1H-isoindole-1,3-(2H)-dione of Formula (E)

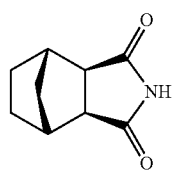

(E)

100 g bicyclo[2.2.1]heptane-2-exo-3-exo-dicarboxylic acid anhydride of Formula (D) and 200 mL tetrahydrofuran were added to round bottom flask at 25 to 35° C. and stirred for 10 min. The reaction mass was cooled to 0 to 5° C. followed by addition of 295 mL 8% aq. ammonia solution. The temperature was raised to 25 to 35° C. and tetrahydrofuran was distilled out under vacuum at 60 to 75° C. The reaction mixture was further heated to 140 to 145° C. The reaction mixture was stirred for 30 min and cooled to 90 to 100° C. 40 mL toluene was added at 0 to 5° C. and stirred for 30 min. The precipitated product was filtered and washed with 200 mL toluene to afford the title compound as bicyclo[2.2.1]heptane-2-exo-3-exo-dicarboximide of Formula (E).

Example-10

Preparation of (3aR,7aR)-4'-benzo[d]isothiazol-3-yl) octahydrospiro[isoindole-2,1'-piperazin]-1'-ium mesylate of Formula (G)

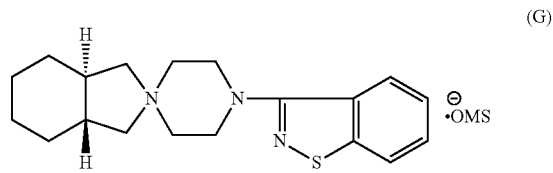

(G)

100 g (1R,2R)-(−)-trans-cyclohexane-1,2-diylbis(methylene)dimethanesulfonate of Formula (B) and 70 g 3-(piperazin-1-yl)benzo[d]isothiazole of Formula (F), 1500 mL acetonitrile and 35 g sodium carbonate and 0.975 g tetrabutyl ammonium hydrogen sulfate were added to round bottom flask at 25° C. to 35° C. and stirred for 10 min. The reaction mixture was heated to 80° to 85° C. for 24 hours. 35 g sodium carbonate and 0.975 g tetrabutyl ammonium hydrogen sulfate and stirred for 21 hours at 80° to 85° C. After completion of the reaction, the reaction mixture was filtered and washed with acetonitrile. The wet-cake was heated with 300 mL acetonitrile at 80° to 85° C. and charcoalized. The reaction mixture was filtered and washed with acetonitrile. The filtrate was distilled under vacuum to remove acetonitrile. The residue was treated with 800 mL acetone and heated to 60° C. for 1 hour followed by cooling. The precipitated product was stirred for 2 hours at 25° C. and filtered. The wet-cake was recrystallized in 50 mL acetone at 60° C. to obtain titled compound (3aR,7aR)-4'-(benzo[d]isothiazol-3-yl)octahydrospiro[isoindole-2,1'-piperazin]-1'-ium mesylate of Formula (G). X-ray powder diffraction pattern (FIG. 5), DSC (FIG. 6).

Example-11

Preparation of Lurasidone Free Base of Formula (H)

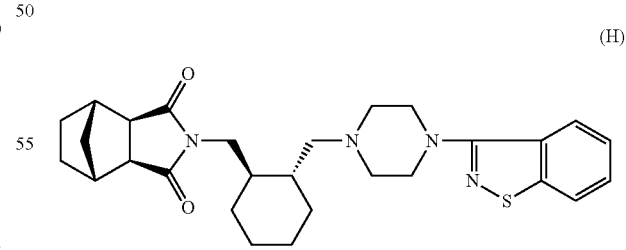

(H)

100 g (3aR,7aR)-4'-(benzo[d]isothiazol-3-yl)octahydrospiro[isoindole-2,1'-piperazin]-1'-ium mesylate of Formula (G) and 55 g (3aS,4R,7S,7aR)-hexahydro-4,7-methano-1H-isoindole-1,3-(2H)-dione of Formula (E), 55 g potassium carbonate, 400 mg dibenzo-18-crown-ether and 1000 mL xylene were added to round bottom flask at 25 to 35° C. The reaction mass was heated to 130° C. to 140° C. and stirred for 3 hours and cooled to 65° C. The reaction mixture was filtered and washed with 50 mL of xylene. The wet-cake was treated with 200 mL xylene at 65° C. for 30 min. The reaction mixture was cooled to 25° C. and filtered. The filtrate was washed with water and separated organic layer was dried over sodium sulfate, charcoalized and distilled under vacuum below 70° C. to obtain residue. The residue was treated with 200 mL isopropanol at 80 to 85° C. The reaction mass cooled to 25 to 35° C. and cooled to 0 to 5° C. The product was filtered and washed with isopropanol to afford the title compound as lurasidone free base of Formula (H). X-ray powder diffraction pattern (FIG. 3), DSC (FIG. 4).

Example-12

Preparation of Lurasidone Hydrochloride of Formula (1)

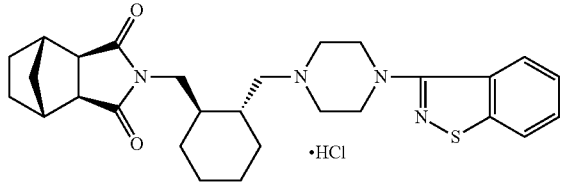

(1)

100 g lurasidone free base of Formula (H) and 3500 mL methanol were added to round bottom flask at 25° C. to 35° C. and heated to 60 to 65° C. for 10 min. To the reaction mass 14% 74.5 g isopropanolic hydrochloric acid was added and stirred for 1 hour at same temperature. The reaction mixture was charcoalized and filtered. The filtrate was distilled to remove methanol under vacuum below 45° C. The residue was again treated with 500 mL methanol at 45° C. and stirred for 30 min. The reaction mixture was cooled to 25° C. The reaction mixture was further cooled to 0 to 5° C. and stirred for 2 hours. The precipitated product was filtered and washed with 100 mL methanol to afford crystalline lurasidone hydrochloride of Formula (1). X-ray powder diffraction pattern (FIG. 1), DSC (FIG. 2).

We claim:
1. A crystalline form of lurasidone free base of Formula (H),

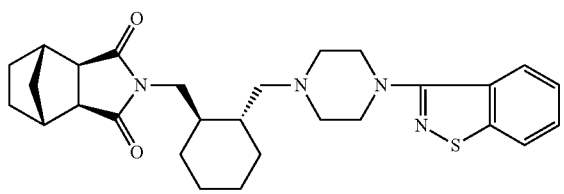

(H)

wherein the crystalline form is characterized by x-ray powder diffraction as depicted in FIG. 3 and differential scanning calorimetry in FIG. 4.

2. The crystalline form as claimed in claim 1 is characterized by X-ray powder diffraction having characteristic peaks at about 11.1°, 13.9°, 15.0°, 15.4°, 16.2°, 16.5°, 17.9°, 19.1°, 19.9°, 20.8°, 22.2° and 26.0°±0.2 degrees 2θ and differential scanning calorimetry having peak at about 151° C.

3. A process for preparing crystalline form of lurasidone free base of Formula (H) as claimed in claim 1,

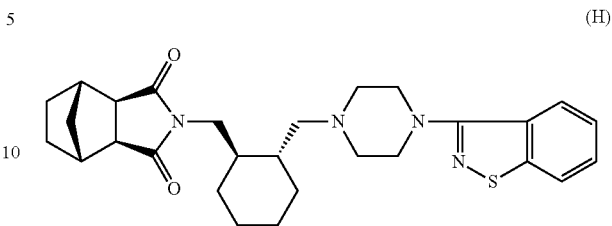

(H)

the process comprising reacting (3aR7aR)-4'-(benzo[d]isothiazol-3-yl)octahydrospiro-[isoindole-2,1'-piperazin]-1'-ium mesylate of Formula (G)

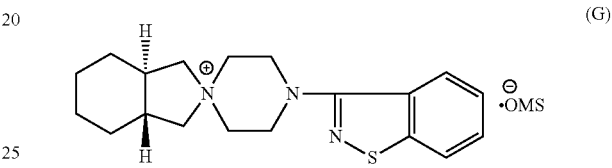

(G)

with bicyclo[2.2.1]heptane-2-exo-3exo-dicacboximide of Formula (E)

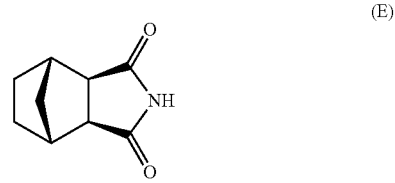 [SMILES: O=C1NC(=O)[C@H]2[C@@H]3CC[C@@H](C3)[C@@H]12]

(E)

in presence of base and phase transfer catalyst in one or more of suitable organic solvent to obtain lurasidone free base and obtaining crystalline form of lurasidone free base of Formula (H) by removal of solvent.

4. The process as claimed in claim 3, wherein the suitable organic solvent comprises one or more of toluene, xylene, ethylbenzene, acetonitrile, ethyl acetate, isopropyl acetate, butyl acetate, acetone, ethyl methyl ketone, methyl isobutyl ketone and the like.

5. The process as claimed in claim 3, wherein the base comprises sodium hydroxide, potassium hydroxide, lithium hydroxide, sodium carbonate, potassium carbonate, sodium bicarbonate, potassium bicarbonate and the like and triethyl amine (TEA), diisopropylethylamine (DIPEA), diisopropylamine (DIPA).

6. The process as claimed in claim 3, wherein the phase transfer catalyst comprises benzyltrimethylammonium chloride, hexadecyltributyl phosphonium bromide, tetrabutyl ammonium hydrogen sulphate, tetrabutylammonium bromide, methyltrioctyl ammonium chloride, crown ethers like dibenzo-18-crown-ether, polyethylene glycols.

7. The process as claimed in claim 3, wherein the crystalline lurasidone free base of Formula (H) is obtained crystallization or recrystallization of obtained compound (H) during reaction in one or more of suitable organic solvent followed by removal of solvent.

8. The process as claimed in claim 7, wherein the suitable solvent of methanol, ethanol, isopropanol, butanol, dimethyl formamide, dimethyl acetamide, acetonitrile, acetone, methyl isobutyl ketone, methyl ethyl ketone, ethyl acetate, isopropyl acetate, butyl acetate.

9. A process for preparation of crystalline lurasidone hydrochloride of Formula (1),

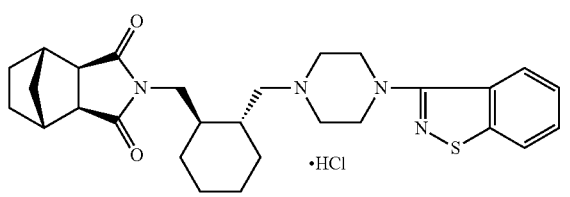

(1)

·HCl the process comprising:
(a) reducing (1R,2R)-(−)-trans-cyclohexane-1,2-dicarboxylic acid with a suitable reducing agent in one or more of suitable organic solvent to obtain (1R,2R)-(−)-trans-cyclohexane-1,2-diyldimethanol of Formula (A);
(b) reacting (1R,2R)-(−)-trans-cyclohexane-1,2-diyldimethanol of Formula (A) with methanesulfonyl chloride in presence of base in one or more of suitable organic solvent to obtain (1R,2R)-(−)-trans-cyclohexane-1,2-diylbis(methylene)dimethanesulfonate of Formula (B);
(c) reacting (1R,2R)-(−)-trans-cyclohexane-1,2-diylbis(methylene)dimethanesulfonate of Formula (B) and 3-(piperazin-1-yl)benzo[d]isothiazole of Formula (F) in presence of base and a phase transfer catalyst in one or more of suitable organic solvent to obtain crystalline form of (3aR,7aR)-4'-(benzo[d]isothiazol-3-yl)octahydrospiro[isoindole-2,1'-piperazin]-1'-ium mesylate of Formula (G);
(d) reacting crystalline form of (3aR,7aR)-4'-(benzo[d]isothiazol-3-yl)octahydrospiro-[isoindole-2,1'-piperazin]-1'-ium mesylate of Formula (G) with (3aS,4R,7S,7aR)-hexahydro-4,7-methano-1H-isoindole-1,3-(2H)-dione of Formula (E) in presence of base and a phase transfer catalyst in one or more of suitable organic solvent to obtain crystalline form of lurasidone free base of Formula (H);
(e) reacting crystalline form of lurasidone free base of Formula (H) with hydrochloric acid source in one or more of suitable organic solvent to obtain lurasidone hydrochloride of Formula (1); and
(f) obtaining crystalline form of lurasidone hydrochloride of Formula (1) by removal of solvent.

10. The process as claimed in claim 9 (a), wherein suitable organic solvent comprises one or more of $C_1$-$C_5$ alcohols, esters, ethers, water, methanol, ethanol, isopropanol, butanol, ethyl acetate, isopropyl acetate, butyl acetate, diethyl ether, diisopropylether, methyltertbutyl ether, tetrahydrofuran, 2-methyltetrahydrofuran, 1,4-dioxane, or a mixture thereof.

11. The process as claimed in claim 9 (a), wherein reducing agent may be selected from the group consisting of sodium borohydide, lithium aluminium hydride, Vitride.

12. The process as claimed in claim 9 (b), wherein the suitable organic solvent comprises one or more of methanol, ethanol, isopropanol, butanol, ethyl acetate, isopropyl acetate, butyl acetate, diethyl ether, diisopropyl ether, methyl tertbutyl ether, tetrahydrofuran, 1,4-dioxane, methylene dichloride, ethylene dichloride, chloroform, chlorobenzene, water or a mixture thereof.

13. The process as claimed in claim 9 (b), wherein the base comprises of sodium hydroxide, potassium hydroxide, lithium hydroxide, sodium carbonate, potassium carbonate, sodium bicarbonate, potassium bicarbonate and the like and triethyl amine (TEA), diisopropylethylamine (DIPEA), diisopropylamine (DIPA).

14. The process as claimed in claim 9 (c), wherein the suitable solvent comprises toluene, xylene, ethylbenzene dimethyl formamide, dimethyl acetamide, acetonitrile, methanol, ethanol, isopropanol, butanol, acetone, methyl isobutyl ketone, methyl ethyl ketone, ethyl acetate, isopropyl acetate, butyl acetate.

15. The process as claimed in claim 9 (c), wherein the base comprises of sodium hydroxide, potassium hydroxide, lithium hydroxide, sodium carbonate, potassium carbonate, sodium bicarbonate, potassium bicarbonate and the like and triethyl amine (TEA), diisopropylethylamine (DIPEA), diisopropyl amine (DIPA).

16. The process as claimed in claim 9 (c), wherein the phase transfer catalyst comprises of benzyltrimethylammonium chloride, hexadecyltributyl phosphonium bromide, tetrabutyl ammonium hydrogen sulphate, tetrabutylammonium bromide, methyltrioctyl ammonium chloride, crown ethers, polyethylene glycols.

17. The process as claimed in claim 9 (d), wherein the suitable organic solvent comprises toluene, xylene, ethylbenzene, acetonitrile, ethyl acetate, isopropyl acetate, butyl acetate, acetone, ethyl methyl ketone, methyl isobutyl ketone and the like.

18. The process as claimed in claim 9 (d), wherein the base comprises of sodium hydroxide, potassium hydroxide, lithium hydroxide, sodium carbonate, potassium carbonate, sodium bicarbonate, potassium bicarbonate and the like and triethyl amine (TEA), diisopropylethyl amine (DIPEA), diisopropylamine (DIPA).

19. The process as claimed in claim 9 (d), wherein the phase transfer catalyst comprises of benzyltrimethylammonium chloride, hexadecyltributyl phosphonium bromide, tetrabutyl ammonium hydrogen sulphate, tetrabutylammonium bromide, methyltrioctyl ammonium chloride, crown ethers like dibenzo-18-crown-ether, polyethylene glycols.

20. The process as claimed in claim 9 (e), wherein the hydrochloric acid source comprises hydrochloric acid, aqueous hydrochloric acid, hydrochloric acid gas, isopropanolic hydrochloride, ethyl acetate hydrochloric acid, acetone hydrochloric acid etc.

21. The process as claimed in claim 9 (e), wherein the suitable organic solvent comprises of toluene, xylene, ethylbenzene dimethyl formamide, dimethyl acetamide, acetonitrile, methanol, ethanol, isopropanol, butanol, acetone, methyl isobutyl ketone, methyl ethyl ketone, ethyl acetate, isopropyl acetate, butyl acetate.

22. The process as claimed in claim 9, wherein the crystalline form of lurasidone hydrochloride of Formula (1) is characterized by X-ray powder diffraction as depicted in FIG. 1 and differential scanning calorimetry as depicted in FIG. 2.

23. The crystalline form of lurasidone hydrochloride as claimed in claim 22 is characterized by X-ray powder diffraction having characteristic peaks at about 11.4°, 13.9°, 15.1°, 15.5°, 16.4°, 17.1°, 17.4°, 19.5°, 20.8°, 21.9°, and 27.4°±0.2 degrees 2θ and differential scanning calorimetry (DSC) having peak at about 282° C.

24. The crystalline lurasidone hydrochloride as claimed in claim 22 having an average particle size in the range of 5 to 300 microns.

25. The crystalline lurasidone hydrochloride as claimed in claim 22 having particle size d90 less than about 100 microns.

26. Microcrystalline lurasidone hydrochloride having particle size d90 less than about 10 microns.

27. A process for the preparation of lurasidone hydrochloride of Formula (1),

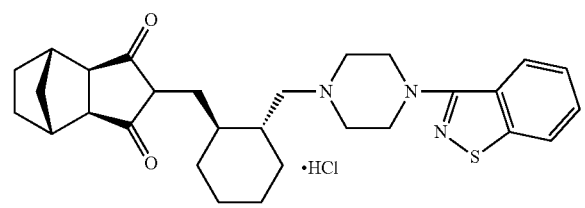

(1)

comprising
(a) reacting (3aR,7aR)-4'-(benzo[d]isothiazol-3-yl)octahydrospiro[isoindole-2,1'-piperazin]-1'-ium mesylate of Formula (G)

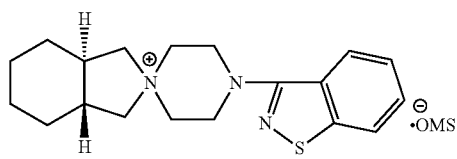

(G)

with (3aS,4R,7S,7aR)-hexahydro-4,7-methano-1H-isoindole-1,3-(2H)-dione of Formula (E)

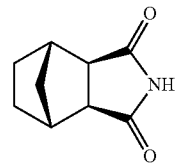

(E)

in the presence of a base and a phase transfer catalyst to obtain lurasidone free base of Formula (H)

(H)

and
(b) reacting the lurasidone free base of Formula (H) with a hydrochloric acid source in one or more organic solvents to obtain lurasidone hydrochloride of Formula (1).

* * * * *